United States Patent
Ngo et al.

(10) Patent No.: US 9,388,153 B2
(45) Date of Patent: Jul. 12, 2016

(54) SECONDARY AMINES AS THERAPEUTIC AGENTS

(71) Applicant: Allergan, Inc., Irvine, CA (US)

(72) Inventors: Vinh X. Ngo, Huntington Beach, CA (US); David W. Old, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/565,817

(22) Filed: Dec. 10, 2014

(65) Prior Publication Data

US 2015/0175567 A1 Jun. 25, 2015

Related U.S. Application Data

(60) Provisional application No. 61/919,557, filed on Dec. 20, 2013.

(51) Int. Cl.
| | |
|---|---|
| *C07D 307/82* | (2006.01) |
| *C07D 311/04* | (2006.01) |
| *C07C 59/72* | (2006.01) |
| *C07C 217/84* | (2006.01) |
| *C07C 233/81* | (2006.01) |
| *A61K 31/136* | (2006.01) |
| *A61K 31/196* | (2006.01) |

(52) U.S. Cl.
CPC ............ *C07D 307/82* (2013.01); *A61K 31/136* (2013.01); *A61K 31/196* (2013.01); *C07C 59/72* (2013.01); *C07C 217/84* (2013.01); *C07C 233/81* (2013.01)

(58) Field of Classification Search
CPC ........................... C07D 307/82; C07D 307/83
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 7,960,369 B2 * | 6/2011 | Fukatsu et al. ................ 514/183 |
| 2007/0129552 A1 | 6/2007 | Donde et al. |

FOREIGN PATENT DOCUMENTS

| EP | 1559422 | 8/2005 |
| EP | 2623490 | 8/2013 |
| WO | 2009-146255 | 12/2009 |

OTHER PUBLICATIONS

Wermuth, Camille. "Molecular Variations Based on Isoteric Replacements." The Practice of Medicinal Chemistry. Academic Press, 1996. pp. 203-237.*
Osol, Arthur, et al., Remington's Handbook, 1980, 16th Ed., pp. I-IX.
Transmittal of the International Search Report & Written Opinion mailed on Mar. 2, 2015 for PCT/US14/69606 filed on Dec. 10, 2014 in the name of Allergan Inc.

* cited by examiner

*Primary Examiner* — Golam M M Shameem
*Assistant Examiner* — Laura Daniel
(74) *Attorney, Agent, or Firm* — Jonathan Bass

(57) ABSTRACT

Compounds such as those represented by Formulas 1-6 can be used in topical liquids, creams, or other dosage forms such as solids, for reducing intraocular pressure, treating glaucoma, growing hair, or other medical uses.

24 Claims, No Drawings

SECONDARY AMINES AS THERAPEUTIC AGENTS

This application claims priority to and the benefit of U.S. Provisional Patent Application No. 61/919,557, filed Dec. 20, 2013, the disclosure of which is hereby incorporated by reference in its entirety.

BACKGROUND

Ocular hypotensive agents are useful in the treatment of a number of various ocular hypertensive conditions, such as post-surgical and post-laser trabeculectomy ocular hypertensive episodes, glaucoma, and as pre-surgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, prostaglandin analogs are the current first line treatment for glaucoma management.

SUMMARY

Some optionally substituted tetrahydrobenzothiophenes, optionally substituted tetrahydrobenzofurans, optionally substituted indolines, optionally substituted dihydroindenes, and optionally substituted tetrahydronaphthylenes can have binding or activity at prostaglandin receptors, such as prostaglandin E receptors, including EP2. These compounds may be useful in treating diseases or conditions such as elevated intraocular pressure, glaucoma, hair loss, etc.

Some embodiments include a compound represented by Formula 1:

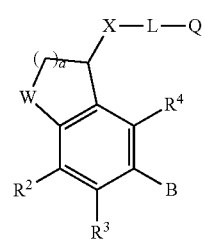

Formula 1 wherein B is optionally substituted phenyl; W is $CH_2$, O, S, or NH; a is 1 or 2; X is $NR^1$ or O; L is $—CH_2O-A$, $—CH_2CH_2-A-$, $—CH=CH-A-$, $-A-OCH_2—$, $-A-CH_2CH_2—$, or $-A-CH=CH—$; A is an optionally substituted interarylene, an optionally substituted interheteroarylene, or $—(CH_2)_3—$; $R^1$ is H, $C_{1-6}$ alkyl, or $COCH_3$; $R^2$, $R^3$, and $R^4$ are independently H, or a substituent having a molecular weight of 15 g/mol to 100 g/mol; and Q is $CO_2R^5$, $CH_2OR^5$, $CONR^5R^6$, or optionally substituted tetrazol-5-yl, wherein $R^5$ and $R^6$ are independently H, $C_{1-6}$ alkyl, $C_{1-6}$ hydroxyalkyl, or optionally substituted phenyl.

Some embodiments include an ophthalmic liquid comprising a compound described herein.

Some embodiments include a solid dosage form comprising a compound described herein.

Some embodiments include a method of reducing intraocular pressure comprising administering a compound described herein.

Some embodiments include a method or growing hair comprising comprising administering a compound described herein.

DETAILED DESCRIPTION

Certain eicosanoids and their derivatives can be used in glaucoma management. Eicosanoids and derivatives include numerous biologically important compounds such as prostaglandins and their derivatives. Prostaglandins can be described as derivatives of prostanoic acid. Prostanoic acid has the following structural formula:

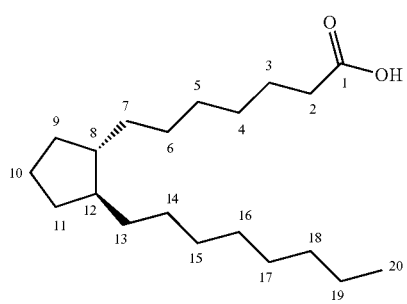

Various types of prostaglandins are classified by the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by or β [e.g. prostaglandin $F_{2\alpha}(PGF_{2\alpha})$]. Changes in the substituents of carbons 9, 10, and 11 can often influence the activity and selectivity of these compounds at the different prostaglandin receptors. Other compounds having more remote structures from natural prostaglandins can also have activity at prostaglandin receptors. For example, some optionally substituted tetrahydrobenzothiophenes, optionally substituted tetrahydrobenzofurans, optionally substituted indolines, optionally substituted dihydroindenes, and optionally substituted tetrahydronaphthylenes can have activity at prostaglandin receptors, such as the prostaglandin EP$_2$ receptor.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom.

Examples of substituents include, but are not limited to, hydrocarbyl, such as alkyl, alkenyl, alkynyl; heteroalkyl, including any alkyl wherein one or more heteroatoms replaces one or more carbon atoms, and some accompanying hydrogen atoms (e.g. N replaces CH, O replaces CH$_2$, Cl replaces CH$_3$, etc.), such as alkoxy, alkylthio, haloalkyl, haloalkoxy, amino, etc.; heteroalkenyl, including any alkenyl wherein one or more heteroatoms replaces one or more carbon atoms, and some accompanying hydrogen atoms, such as acyl, acyloxy, thiocarbonyl, alkylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any alkynyl wherein one or more heteroatoms replaces one or more carbon atoms, and some accompanying hydrogen atoms, such as cyano, thiocyanato, cyanato; aryl; heteroaryl; hydroxy; aryloxy; thiol; halo; S-sulfonamido; N-sulfonamido; nitro, silyl; sulfonyl; trihalomethanesulfonyl; trihalomethanesulfonamido; etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by —|, attachment may occur at any position normally occupied by a hydrogen atom.

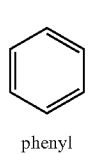
phenyl

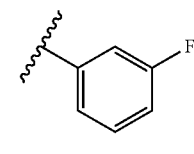
3-fluorophenyl

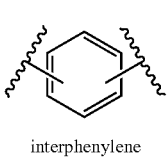
interphenylene

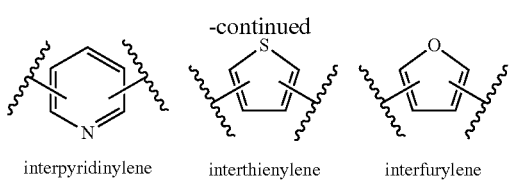
interpyridinylene   interthienylene   interfurylene

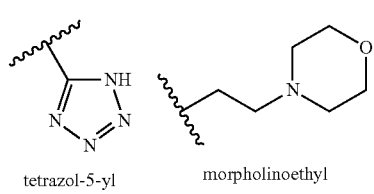
tetrazol-5-yl       morpholinoethyl

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include C$_{1-10}$ linear alkyl, such as methyl (—CH$_3$), ethyl (—CH$_2$CH$_3$), n-propyl (—CH$_2$CH$_2$CH$_3$), n-butyl (—CH$_2$CH$_2$CH$_2$CH$_3$), n-pentyl (—CH$_2$CH$_2$CH$_2$CH$_2$CH$_3$), n-hexyl (—CH$_2$CH$_2$CH$_2$CH$_2$CH$_2$CH$_3$), etc.; C$_{3-10}$ branched alkyl, such as C$_3$H$_7$ (e.g. iso-propyl), C$_4$H$_9$ (e.g. branched butyl isomers), C$_5$H$_{11}$ (e.g. branched pentyl isomers), C$_6$H$_{13}$ (e.g. branched hexyl isomers), C$_7$H$_{15}$ (e.g. heptyl isomers), etc.; C$_{3-10}$ cycloalkyl, such as C$_3$H$_5$ (e.g. cyclopropyl), C$_4$H$_7$ (e.g. cyclobutyl isomers such as cyclobutyl, methylcyclopropyl, etc.), C$_5$H$_9$ (e.g. cyclopentyl isomers such as cyclopentyl, methylcyclobutyl, dimethylcyclopropyl, etc.) C$_6$H$_{11}$ (e.g. cyclohexyl isomers), C$_7$H$_{13}$ (e.g. cycloheptyl isomers), etc.; and the like.

As used herein the term "interarylene" has the broadest meaning generally understood in the art, and may include, —Ar—, wherein Ar is an aromatic ring or aromatic ring system, such as interphenylene.

The term "interheteroarylene" also has the meaning understood by a person of ordinary skill in the art, and includes an "interarylene" which has one or more heteroatoms in the ring or ring system, such as interpyridinylene, interfurylene, interthienylene, interoxazolylene, interthiazolylene, interimidazolylene, etc.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, such as in Formulas 1-6, a name or structural depiction includes any stereoisomer or any mixture of stereoisomers.

Formula 2

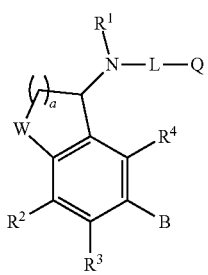

Formula 3

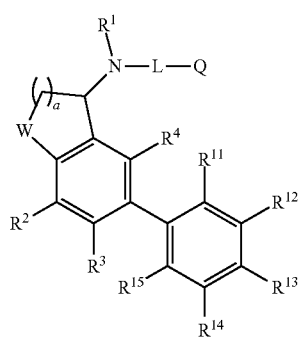

Formula 4

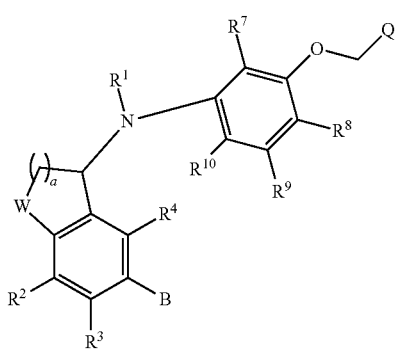

Formula 5

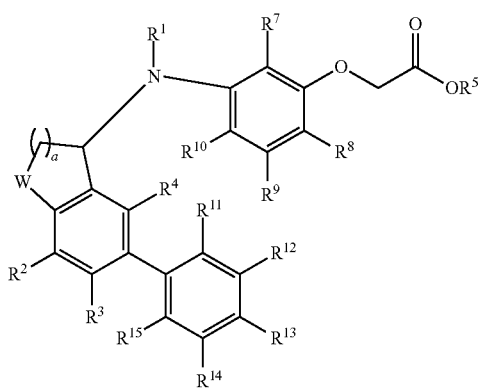

Formula 6

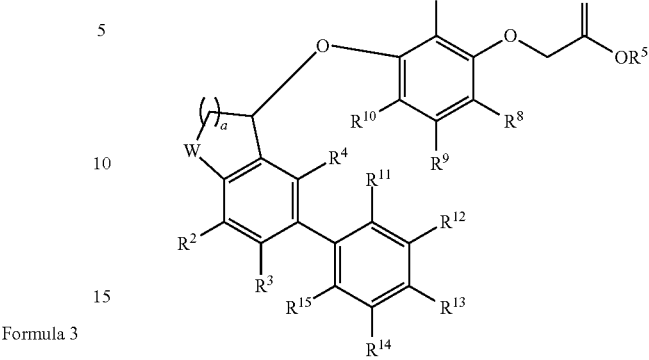

With respect to any relevant structural representation, such as Formula 1, 2, or 4, B is optionally substituted phenyl. If B is substituted, it may have 1, 2, 3, 4, or 5 substituents. Any substituent may be included on the phenyl. In some embodiments, some or all of the substituents on the phenyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$ alkoxyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments a substituent of B is $C_{1-12}$ alkyl, $C_{1-12}$ hydroxyalkyl, F, or Cl. In some embodiments, B is fluorophenyl, such as 3-fluorophenyl. In some embodiments, B is:

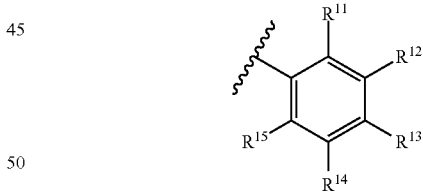

With respect to any relevant structural representation, such as Formula 1, 2, 3, 4, 5, or 6, W is $CH_2$, O, S, or NH. In some embodiments, W is $CH_2$. In some embodiments, W is O.

With respect to any relevant structural representation, such as Formula 1, 2, 3, 4, 5, or 6, a is 1 or 2. In some embodiments, a is 1. In some embodiments, a is 2.

With respect to any relevant structural representation, such as Formula 1, X can be $NR^1$ or O. In some embodiments, X is $NR^1$. In some embodiments, X is O.

With respect to Formula 1, in some embodiments, X is O and B is substituted phenyl.

With respect to any relevant structural representation, such as Formula 2, 3, 4, or 5, $R^1$ is H, $C_{1-6}$ alkyl, or $COCH_3$. In some embodiments, $R^1$ is $C_{1-3}$ alkyl or $COCH_3$. In some embodiments, $R^1$ is H. In some embodiments, $R^1$ is methyl. In some embodiments, $R^1$ is ethyl. In some embodiments, $R^1$ is $COCH_3$.

With respect to any relevant structural representation, such as Formula 1, 2, 3, 4, 5, or 6, $R^2$ is H, or any substituent, such as a substituent having a molecular weight of 15 g/mol to 100 g/mol. In some embodiments, $R^2$ is H, $C_{1-6}$ alkyl, CN, $NO_2$, $NH_2$, $NHCH_3$, $N(CH_3)_2$, OH, $C_{1-4}$—O-alkyl, CHO, $COCH_3$, $CF_3$, F, Cl, or Br. In some embodiments, $R^2$ is H.

With respect to any relevant structural representation, such as Formula 1, 2, 3, 4, 5, or 6, $R^3$ is H, or any substituent, such as a substituent having a molecular weight of 15 g/mol to 100 g/mol. In some embodiments, $R^3$ is H, $C_{1-6}$ alkyl, CN, $NO_2$, $NH_2$, $NHCH_3$, $N(CH_3)_2$, OH, $C_{1-4}$—O-alkyl, CHO, $COCH_3$, $CF_3$, F, Cl, or Br. In some embodiments, $R^3$ is H.

With respect to any relevant structural representation, such as Formula 1, 2, 3, 4, 5, or 6, $R^4$ is H, or any substituent, such as a substituent having a molecular weight of 15 g/mol to 100 g/mol. In some embodiments, $R^4$ is H, $C_{1-6}$ alkyl, CN, $NO_2$, $NH_2$, $NHCH_3$, $N(CH_3)_2$, OH, $C_{1-4}$—O-alkyl, CHO, $COCH_3$, $CF_3$, F, Cl, or Br. In some embodiments, $R^4$ is H.

With respect to any relevant structural representation, such as Formula 1, 2, or 3, L is —$CH_2$O-A-, —$CH_2CH_2$-A-, —CH=CH-A-, -A-$OCH_2$—, -A-$CH_2CH_2$—, or -A-CH=CH—. In some embodiments, L is -A-$OCH_2$—. A is an optionally substituted interarylene, such as optionally substituted interphenylene; an optionally substituted interheteroarylene, such as optionally substituted interpyridinylene, optionally substituted interthienylene, optionally substituted interfurylene, etc.; or —$(CH_2)_3$—. In some embodiments, A is unsubstituted. If A is substituted, an interphenylene may have 1, 2, 3, or 4 substituents, an interpyridinylene may have 1, 2, or 3 substituents, and an interthienylene or interfurylene may have 1 or 2 substituents. In some embodiments, some or all of the substituents on B may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$ alkoxyl; $C_{1-20}$ hydroxyalkyl; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, A is unsubstituted, or any substituents are F, Cl, Br, $CH_3$, $OCH_3$, $NH_2$, or $CF_3$. In some embodiments A is substituted or unsubstituted interphenylene. In some embodiments, A is:

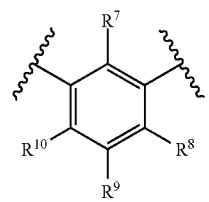

With respect to any relevant structural representation, such as Formula 1, 2, 3, or 4, Q is $CO_2R^5$, $CH_2OR^5$, $CONR^5R^6$, or optionally substituted tetrazol-5-yl.

For any relevant Q group, $R^5$ is H; $C_{1-6}$ alkyl, such as methyl, ethyl, propyl, isopropyl, butyl isomers, etc.; $C_{1-6}$ hydroxyalkyl, such as 2-hydroxyethyl; or optionally substituted phenyl.

For any relevant Q group, $R^6$ is H; $C_{1-6}$ alkyl, such as methyl, ethyl, propyl, isopropyl, butyl isomers, etc.; $C_{1-6}$ hydroxyalkyl, such as 2-hydroxyethyl; morpholinoalkyl, such as 2-morpholinoethyl; or optionally substituted phenyl.

For any relevant Q group, if the tetrazol-5-yl is substituted, it may have 1 substituent, which can be any substituent, but may typically be a substituent having a carbon atom that directly attaches to the tetrazol-5-yl, such as $C_{1-6}$ alkyl (including methyl, ethyl, n-propyl, isopropyl, etc.), optionally substituted phenyl, etc.

With respect to any relevant structural representation, such as Formula 1, 2, 3, or 4, in some embodiments, Q is $CO_2R^5$. In some embodiments, Q is $CO_2H$, $CO_2CH_3$, $CO_2CH_2CH_3$, $CO_2CH(CH_3)_2$, or $CO_2CH_2CH_2OH$. In some embodiments, Q is $CH_2OH$.

With respect to any relevant structural representation, such as Formula 1, 2, 3, 4, 5, or 6, in some embodiments, W is $CH_2$ and a is 1.

With respect to any relevant structural representation, such as Formula 1, 2, 3, 4, 5, or 6, in some embodiments, W is O and a is 1.

With respect to any relevant structural representation, such as Formula 1, 2, 3, 4, 5, or 6, in some embodiments, W is $CH_2$ and a is 2.

With respect to any relevant structural representation, such as Formula 3, 4, or 5, $R^7$, $R^8$, $R^9$, and $R^{10}$ may independently be H or any substituent, such as a substituent having from 0 to 6 carbon atoms and from 0 to 5 heteroatoms, wherein each heteroatom is independently: O, N, S, F, Cl, Br, or I; and/or having a molecular weight of 15 g/mol to 300 g/mol, or 15 g/mol to 150 g/mol. In some embodiments, $R^7$, $R^8$, $R^9$, and $R^{10}$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^7$, $R^8$, $R^9$, and $R^{10}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

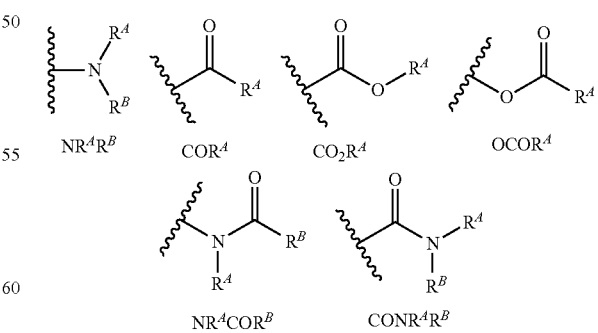

Each $R^A$ may independently be H, or $C_{1-12}$ alkyl, including: linear or branched alkyl having a formula $C_xH_{2x+1}$, or cycloalkyl having a formula $C_xH_{2x-1}$, wherein x is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

Each $R^B$ may independently be H, or $C_{1-12}$ alkyl, including: linear or branched alkyl having a formula $C_aH_{a+1}$; or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $CH_{1-3}$ alkyl. In some embodiments, $R^B$ may be H or $CH_3$. In some embodiments, $R^B$ may be H.

With respect to any relevant structural representation, such as Formula 3, 4, or 5, in some embodiments, $R^7$ is H, F, Cl, or $CH_3$. In some embodiments, $R^7$ is H. Additionally, for any embodiments recited in this paragraph, $R^8$, $R^9$, and $R^{10}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 4, or 5, in some embodiments, $R^8$ is H, F, Cl, or $CH_3$. In some embodiments, $R^8$ is H. Additionally, for any embodiments recited in this paragraph, $R^7$, $R^9$, and $R^{10}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 4, or 5, in some embodiments, $R^9$ is H, F, Cl, or $CH_3$. In some embodiments, $R^9$ is H. Additionally, for any embodiments recited in this paragraph, $R^7$, $R^8$, and $R^{10}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 4, or 5, in some embodiments, $R^{10}$ is H, F, Cl, or $CH_3$. In some embodiments, $R^{10}$ is H. Additionally, for any embodiments recited in this paragraph, $R^7$, $R^8$, and $R^9$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 4, or 5, in some embodiments, $R^7$ and $R^8$ are H. In some embodiments, $R^7$ and $R^9$ are H. In some embodiments, $R^7$ and $R^{10}$ are H. In some embodiments, $R^7$, $R^8$, $R^9$, and $R^{10}$ are H.

With respect to any relevant structural representation, such as Formula 3, 5, or 6, $R^{11}$, $R^{12}$, $R^{13}$, $R^{14}$ and $R^{15}$ independently be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol, or 15 g/mol to 150 g/mol. In some embodiments, $R^{11}$, $R^{12}$, $R^{13}$, $R^{14}$ and $R^{15}$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{11}$, $R^{12}$, $R^{13}$, $R^{14}$ and $R^{15}$ are independently H; F; Cl; Br; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

With respect to Formula 3, 5, or 6, in some embodiments at least one of $R^{11}$, $R^{12}$, $R^{13}$, $R^{14}$ and $R^{15}$ is not H. In some embodiments, $R^{11}$ is not H. In some embodiments, $R^{12}$ is not H. In some embodiments, $R^{13}$ is not H. In some embodiments, $R^{14}$ is not H. In some embodiments, $R^{15}$ is not H.

With respect to any relevant structural representation, such as Formula 3, 5, or 6, in some embodiments $R^{11}$ is H, F, Cl, $C_{1-10}$ alkyl, or $C_{1-10}$ hydroxyalkyl. In some embodiments, $R^{11}$ is H. Additionally, for any embodiments recited in this paragraph, $R^{12}$, $R^{13}$, $R^{14}$, and $R^{15}$ can independently be: $R^A$, F, Cl, Br, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 5, or 6, in some embodiments $R^{12}$ is H, F, Cl, Br, $C_{1-10}$ alkyl, or $C_{1-10}$ hydroxyalkyl. In some embodiments, $R^{12}$ is H. In some embodiments, $R^{12}$ is F. Additionally, for any embodiments recited in this paragraph, $R^{11}$, $R^{13}$, $R^{14}$, and $R^{15}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 5, or 6, in some embodiments $R^{13}$ is H, F, Cl, $C_{1-10}$ alkyl, or $C_{1-10}$ hydroxyalkyl. In some embodiments, $R^{13}$ is H. Additionally, for any embodiments recited in this paragraph, $R^{11}$, $R^{12}$, $R^{14}$, and $R^{15}$ can independently be: $R^A$, F, Cl, Br, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 5, or 6, in some embodiments $R^{14}$ is H, F, Cl, $C_{1-10}$ alkyl, or $C_{1-10}$ hydroxyalkyl. In some embodiments, $R^{14}$ is H. Additionally, for any embodiments recited in this paragraph, $R^{11}$, $R^{12}$, $R^{13}$, and $R^{15}$ can independently be: $R^A$, F, Cl, Br, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 3, 5, or 6, in some embodiments $R^{15}$ is H, F, Cl, $C_{1-10}$ alkyl, or $C_{1-10}$ hydroxyalkyl. In some embodiments, $R^{15}$ is H. Additionally, for any embodiments recited in this paragraph, $R^{11}$, $R^{12}$, $R^{13}$, and $R^{14}$ can independently be: $R^A$, F, Cl, Br, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

Some embodiments include optionally substituted 2-(3-((6-(3-fluorophenyl)-2,3-dihydro-1H-inden-1-yl)amino)phenoxy)acetic acid; optionally substituted 2-(3-(N-(6-(3-fluorophenyl)-2,3-dihydro-1H-inden-1-yl)acetamido)phenoxy)acetic acid; optionally substituted 2-(3-((6-(3-fluorophenyl)-2,3-dihydro-1H-inden-1-yl)(methyl)amino)phenoxy)acetic acid; optionally substituted 2-(3-(ethyl(6-(3-fluorophenyl)-2,3-dihydro-1H-inden-1-yl)amino)phenoxy)acetic acid; optionally substituted 2-(3-((6-(3-fluorophenyl)-2,3-dihydro-1H-inden-1-yl)oxy)phenoxy)acetic acid; optionally substituted 2-(3-((7-(3-fluorophenyl)-1,2,3,4-tetrahydronaphthalen-1-yl)amino)phenoxy)acetic acid; optionally substituted 2-(3-((7-(3-fluorophenyl)-1,2,3,4-tetrahydronaphthalen-1-yl)amino)phenoxy)ethanol; or optionally substituted 2-(3-((5-(3-fluorophenyl)-2,3-dihydrobenzofuran-3-yl)oxy)phenoxy)acetic acid.

Some embodiments include 2-(3-((6-(3-fluorophenyl)-2,3-dihydro-1H-inden-1-yl)amino)phenoxy)acetic acid; 2-(3-(N-(6-(3-fluorophenyl)-2,3-dihydro-1H-inden-1-yl)acetamido)phenoxy)acetic acid; 2-(3-((6-(3-fluorophenyl)-2,3-dihydro-1H-inden-1-yl)(methyl)amino)phenoxy)acetic acid; 2-(3-(ethyl(6-(3-fluorophenyl)-2,3-dihydro-1H-inden-1-yl)amino)phenoxy)acetic acid; 2-(3-((6-(3-fluorophenyl)-2,3-dihydro-1H-inden-1-yl)oxy)phenoxy)acetic acid; 2-(3-((7-(3-fluorophenyl)-1,2,3,4-tetrahydronaphthalen-1-yl)amino)phenoxy)acetic acid; 2-(3-((7-(3-fluorophenyl)-1,2,3,4-tetrahydronaphthalen-1-yl)amino)phenoxy)ethanol; or 2-(3-((5-(3-fluorophenyl)-2,3-dihydrobenzofuran-3-yl)oxy)phenoxy)acetic acid.

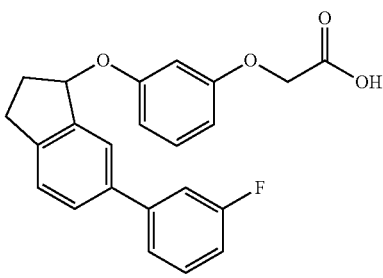
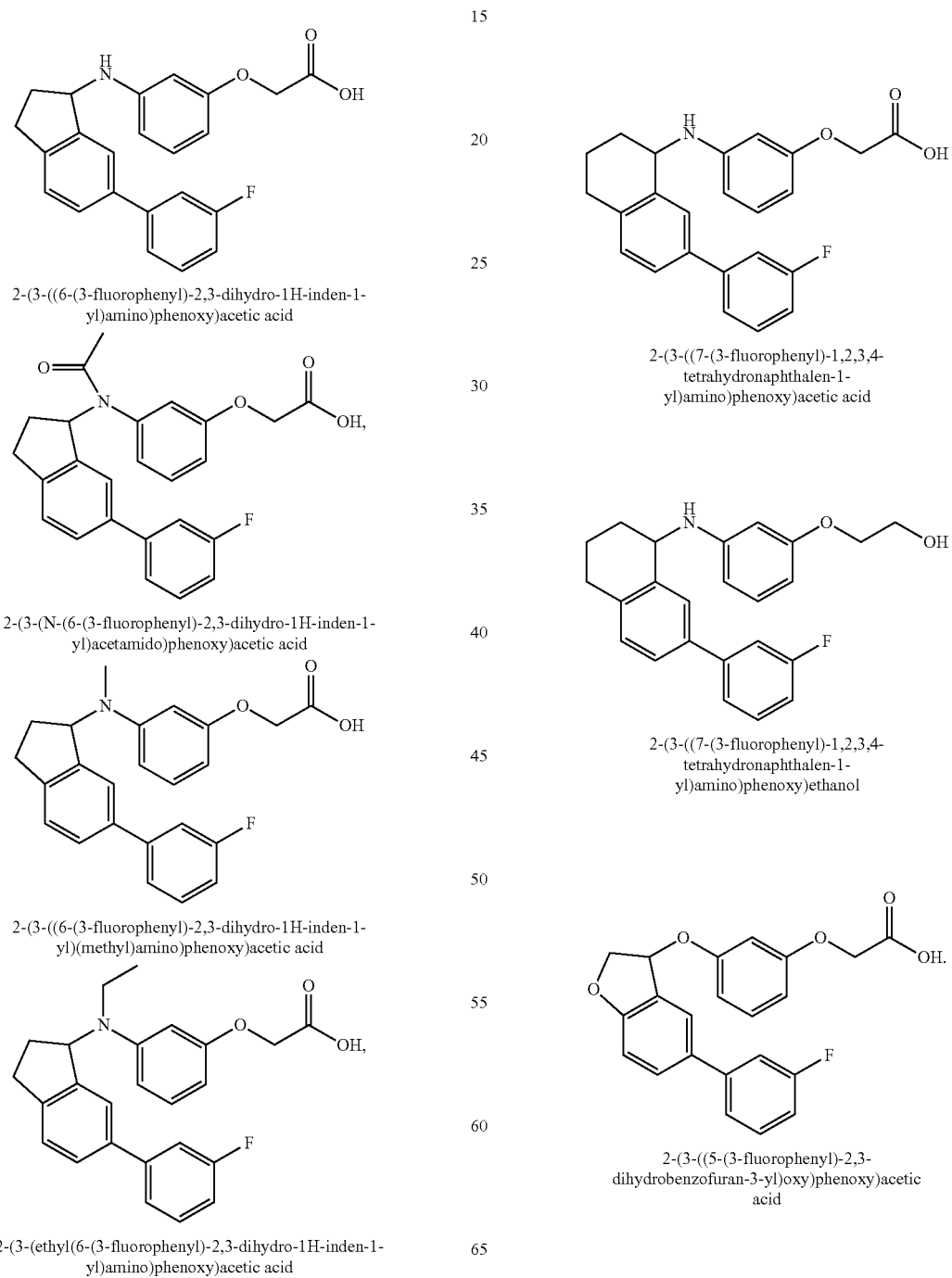

With respect to Formula 1, in some embodiments the compound is not

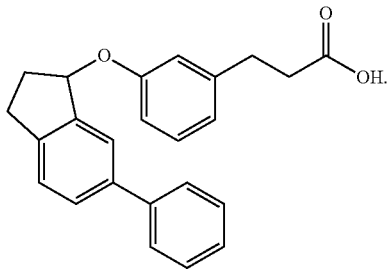 [SMILES: O=C(O)CCc1cccc(OC2CCc3ccc(-c4ccccc4)cc32)c1]

In some embodiments, a compound described herein, such as a compound of any of Formulas 1-6, optionally substituted tetrahydrobenzothiophenes, optionally substituted tetrahydrobenzofurans, optionally substituted indolines, optionally substituted dihydroindenes, and optionally substituted tetrahydronaphthylenes, optionally substituted 2-(3-((6-(3-fluorophenyl)-2,3-dihydro-1H-inden-1-yl)amino)phenoxy) acetic acid; optionally substituted 2-(3-(N-(6-(3-fluorophenyl)-2,3-dihydro-1H-inden-1-yl)acetamido) phenoxy)acetic acid; optionally substituted 2-(3-((6-(3-fluorophenyl)-2,3-dihydro-1H-inden-1-yl)(methyl)amino) phenoxy)acetic acid; optionally substituted 2-(3-(ethyl(6-(3-fluorophenyl)-2,3-dihydro-1H-inden-1-yl)amino)phenoxy) acetic acid; optionally substituted 2-(3-((6-(3-fluorophenyl)-2,3-dihydro-1H-inden-1-yl)oxy)phenoxy)acetic acid; optionally substituted 2-(3-((7-(3-fluorophenyl)-1,2,3,4-tetrahydronaphthalen-1-yl)amino)phenoxy)acetic acid; optionally substituted 2-(3-((7-(3-fluorophenyl)-1,2,3,4-tetrahydronaphthalen-1-yl)amino)phenoxy)ethanol; or optionally substituted 2-(3-((5-(3-fluorophenyl)-2,3-dihydrobenzofuran-3-yl)oxy)phenoxy)acetic acid, (referred to hereafter as a "subject compound") binds to a prostaglandin receptor, such as a prostaglandin EP2 receptor. The subject compound may be an agonist or an antagonist of the receptor.

In some embodiments, a subject compound binds to a prostaglandin EP2 receptor with a binding EC50 value of less than about 10 µM, about 1 µM, about 200 nM, about 100 nM, about 50 nM, about 20 nM, about 10 nM, or about 1 nM, and may have EC50 value as low as 10 pM, 1 pM, or less.

In some embodiments, a subject compound is a prostaglandin receptor agonist. For example, a subject compound may be an agonist of a prostaglandin EP2 receptor with a functional EC50 value of less than about 10 µM, about 1 µM, about 200 nM, about 100 nM, about 50 nM, about 20 nM, about 10 nM, or about 1 nM, and may have an EC50 value as low as 10 pM, 1 pM, or less.

In some embodiments, a subject compound is more active at the prostaglandin EP2 receptor than at any other prostaglandin receptor. For example, a subject compound may have a functional or binding EC50 that is at least about 10 times, about 100 times, or at least about 1000 times lower, and may be up to 100,000 times lower, than the functional or binding EC50 for the same compound at any other prostaglandin receptor.

Subject compounds can be used for reducing intraocular pressure. Reduction of intraocular pressure has been shown to delay or prevent the onset of glaucoma, such as primary open angle glaucoma, and to delay or prevent further vision loss in patients with primary open angle glaucoma. Thus, subject compounds are also useful for treating glaucoma.

Subject compounds can also be used for growing hair, including one or more of: increasing the number of individual hairs, increasing the length of individual hairs, and increasing the width or thickness of individual hairs. Subject compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

For the purposes of this disclosure, "treat," "treating," or "treatment" includes use of a compound, composition, therapeutically active agent, or drug in the diagnosis, cure, mitigation, treatment, or prevention of disease or other undesirable condition.

A pharmaceutically acceptable salt includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A prodrug includes a compound which is converted to a therapeutically active compound after administration, such as by hydrolysis of an ester group or some other biologically labile group. Ester prodrugs of the subject compounds are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. Some examples of useful esters can include an alkyl ester, a hydroxyalkyl ester, a morpholinoalkyl ester, an aryl ester, or a heteroaryl ester.

Those skilled in the art will readily understand that for administration or the manufacture of medicaments, subject compounds can be admixed with pharmaceutically acceptable excipients. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Liquid pharmaceutically administrable dosage forms can, for example, comprise a solution or suspension of one or more of the subject compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the subject compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day.

A liquid which is ophthalmically acceptable includes a liquid that is formulated such that it can be administered topically to the eye. The comfort can be a consideration, although sometimes formulation considerations (e.g. drug stability) may necessitate less than optimal comfort. In the case that comfort is not ideal, the liquid can be formulated such that the liquid is tolerable to the patient for topical ophthalmic use. Additionally, an ophthalmically acceptable liquid can be packaged for single use, or contain a preservative to prevent contamination over multiple uses.

For ophthalmic application, solutions or medicaments are often prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

Preservatives that may be used in pharmaceutical compositions include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used in an ophthalmically acceptable liquid. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the an ophtalmically acceptable liquids include, but are not limited to, sodium metabisulfite, sodium thiosulfate, acetylcysteine, butylated hydroxyanisole and butylated hydroxytoluene.

Other excipient components which may be included in ophthalmic preparations are chelating agents. A useful chelating agent is edetate disodium, although other chelating agents may also be used in place or in conjunction with it.

Some ophthalmically acceptable liquid dosage forms include ingredients having the following amounts:

| Ingredient | Amount (% w/v) |
| --- | --- |
| subject compound | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing subject compounds are employed. Topical formulations can include a pharmaceutical carrier, co-solvent, emulsifier, penetration enhancer, preservative system, or emollient.

The actual dose of a subject compound depends on factors such as the specific compound, and on the condition to be treated; the selection of the appropriate dose is well within the skill of the skilled artisan with the benefit of this disclosure.

For treatment of diseases affecting the eye including glaucoma, subject compounds can be administered topically, periocularly, intraocularly, or by any other effective means known in the art.

In one embodiment, the subject compounds can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The subject compounds can be used to stimulate, such as the conversion of vellus hair to growth as terminal hair, as well as increasing the rate of growth of terminal hair.

The subject compounds can also be used to stimulate growth of eye lashes. Application of a subject compound to an eye or an eyelid can result in lashes that are longer and have a fuller, denser appearance in the treated eye. The changes in the lashes may be apparent on gross inspection. Possible changes to lashes can include increased length of lashes, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation from the skin surface.

In one embodiment, the subject compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more subject compounds and a dermatologically compatible carrier. Effective amounts of the subject compounds may be determined by one of ordinary skill in the art, but will vary depending on the compound employed, frequency of application and desired result. The subject compound will generally range from about 0.0000001 to about 50% by weight; about 0.001 to about 50% by weight; or about 0.1 to about 30% by weight of the dermatological composition.

In one embodiment, the application of the subject compounds for stimulation of hair growth finds applications in mammalian species, including both humans and animals. In humans, the subject compounds can be applied for example, to the scalp, face beard, head, pubic area, upper lip, eyebrows, and eyelids. In animal raised for their pelts, e.g., mink, the subject compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed with respect to hair growth relates to the use of a subject compound incorporated in a suitable pharmaceutical carrier, and applied at the site of thinning hair or baldness for exertion of local action. Accordingly, such topical compositions include those pharmaceutical forms in which the subject compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the subject compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, at least three months, or at least six months.

For topical use on the eyelids or eyebrows, the subject compounds can be formulated in aqueous solutions, creams, ointments, or oils exhibiting physiologically acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of subject compound for treatment of the eyelid may be about 0.1 ng to about 100 mg per eyelid.

For topical use on the skin and scalp, the subject compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betaine, chlorhexidine, benzalkonium chloride, and the like. Various matrices for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the subject compound and the formulation. To achieve the daily amount of medication depending on the formulation, the subject compound may be administered once or several times daily with or without antioxidants.

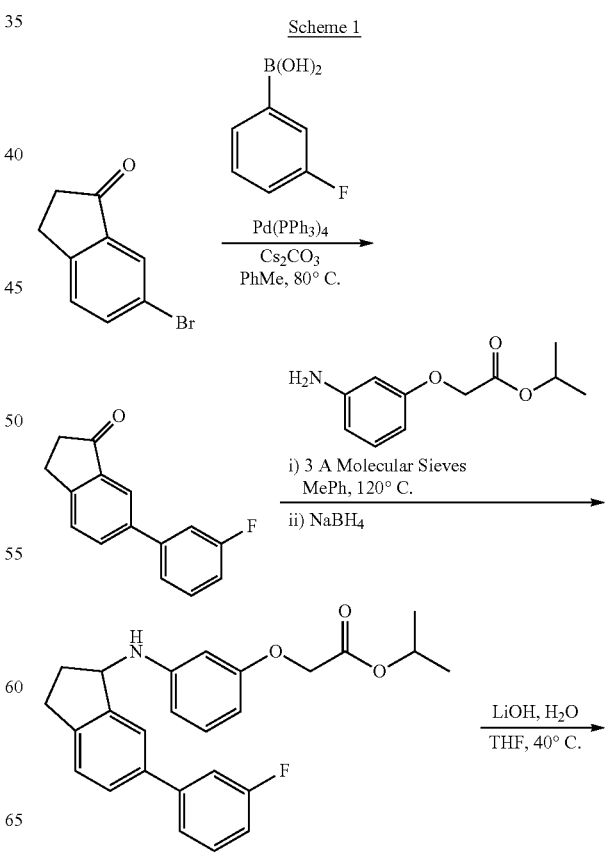

Scheme 1

-continued

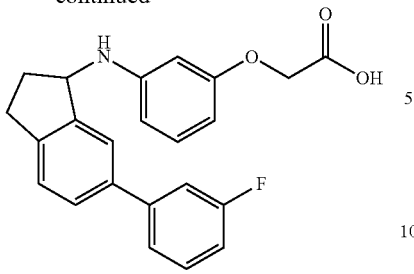

EXAMPLE 1

2-(3-((6-(3-Fluorophenyl)-2,3-dihydro-1H-inden-1-yl)amino)phenoxy)acetic acid

Step 1.
6-(3-Fluorophenyl)-2,3-dihydro-1H-inden-1-one

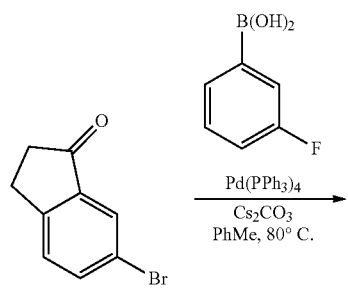

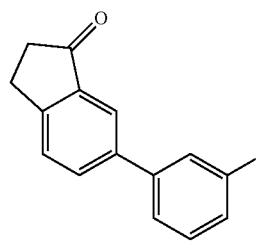

Cesium carbonate (618 mg, 1.90 mmol) was added to a solution of 6-bromo-2,3-dihydro-1H-inden-1-one (200 mg, 0.948 mmol), (3-fluorophenyl)boronic acid (265 mg, 1.90 mmol) and toluene (20 mL) in a 50 mL Schlenk tube at room temperature. A nitrogen atmosphere was established by evacuating and refilling with nitrogen (3×), then tetrakis (triphenylphosphine)palladium (0) (11 mg, 0.001 mmol) was added to the reaction. The flask was sealed and heated in a 80° C. oil bath overnight. The resulting mixture was cooled to room temperature. The reaction was then diluted with ethyl acetate and filtered through celite. Ethyl acetate (30 mL) was used to wash the flask and the combined organic filtrate was concentrated in vacuo. The resulting crude residue was purified on a Teledyne-Isco combiflash machine (40 g column, hexanes→100% ethyl acetate/hexanes, gradient) to afford 174 mg (81%) of 6-(3-fluorophenyl)-2,3-dihydro-1H-inden-1-one.

Step 2. Isopropyl 2-(3-((6-(3-Fluorophenyl)-2,3-Dihydro-1H-Inden-1-yl)amino)phenoxy)acetate

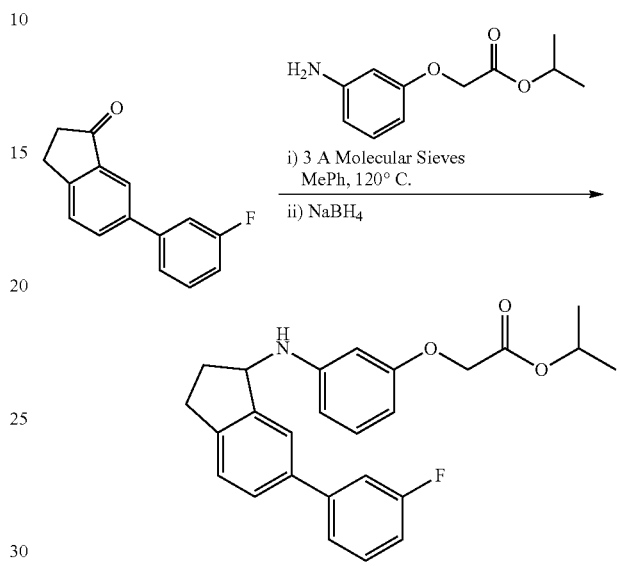

Approximately forty oven dried 3 Å molecular sieves were added to a solution of 6-(3-fluorophenyl)-2,3-dihydro-1H-inden-1-one (66 mg, 0.292 mmol) and isopropyl 2-(3-aminophenoxyl)acetate (122 mg, 0.583 mmol) in toluene (3 mL) at room temperature. The reaction was heated in a 120° C. oil bath and allowed to stir overnight for approximately 16 hours. The reaction was cooled to room temperature and sodium borohydride (44 mg, 1.2 mmol) was added. The solution was stirred for 4 hours at room temperature. The reaction was quenched with saturated aqueous NaHCO$_3$ (50 mL) and extracted with ethyl acetate (3×50 mL). The combined organic extracts were dried (Na$_2$SO$_4$), filtered and concentrated. The resulting crude residue was purified by combiflash (12 g column, hexanes→100% ethyl acetate/hexanes, gradient) to afford 25 mg (20%) of isopropyl 2-(3-((6-(3-fluorophenyl)-2,3-dihydro-1H-inden-1-yl)amino)phenoxy)acetate.

Step 3. 2-(3-((6-(3-Fluorophenyl)-2,3-dihydro-1H-inden-1-yl)amino)phenoxy)acetic acid

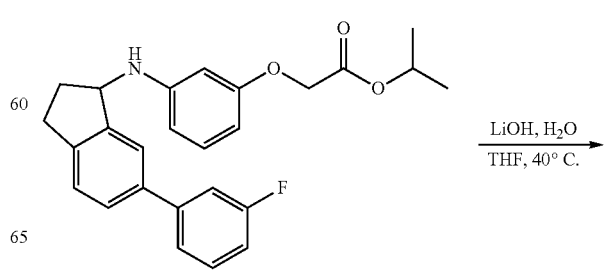

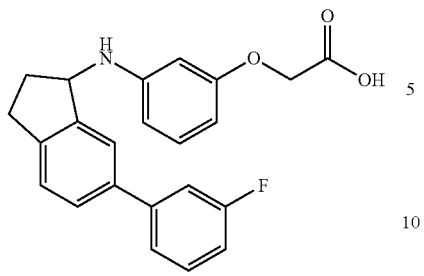

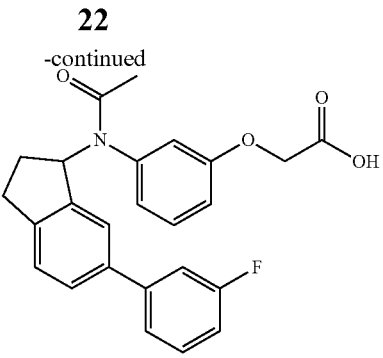

Aqueous lithium hydroxide (1 N, 1 mL, 1 mmol) was added to a solution of isopropyl 2-(3-((6-(3-fluorophenyl)-2,3-dihydro-1H-inden-1-yl)amino)phenoxy)acetate (25 mg, 0.06 mmol) in THF (1 mL) in a scintillation vial. The vial was sealed and heated at 40° C. After 24 h, the reaction mixture was allowed to cool and the volatiles were concentrated. The residue was acidified with hydrochloric acid (1 N, 1 mL) and extracted with ethyl acetate (3×2 mL). The combined organic extracts were dried ($Na_2SO_4$), filtered and concentrated to afford 17 mg (76%) of the title compound.

EXAMPLE 2

2-(3-(N-(6-(3-Fluorophenyl)-2,3-dihydro-1H-inden-1-yl)acetamido)phenoxy)acetic acid Step 1. Methyl 2-(3-((6-(3-fluorophenyl)-2,3-dihydro-1H-inden-1-yl)amino)phenoxy)acetate

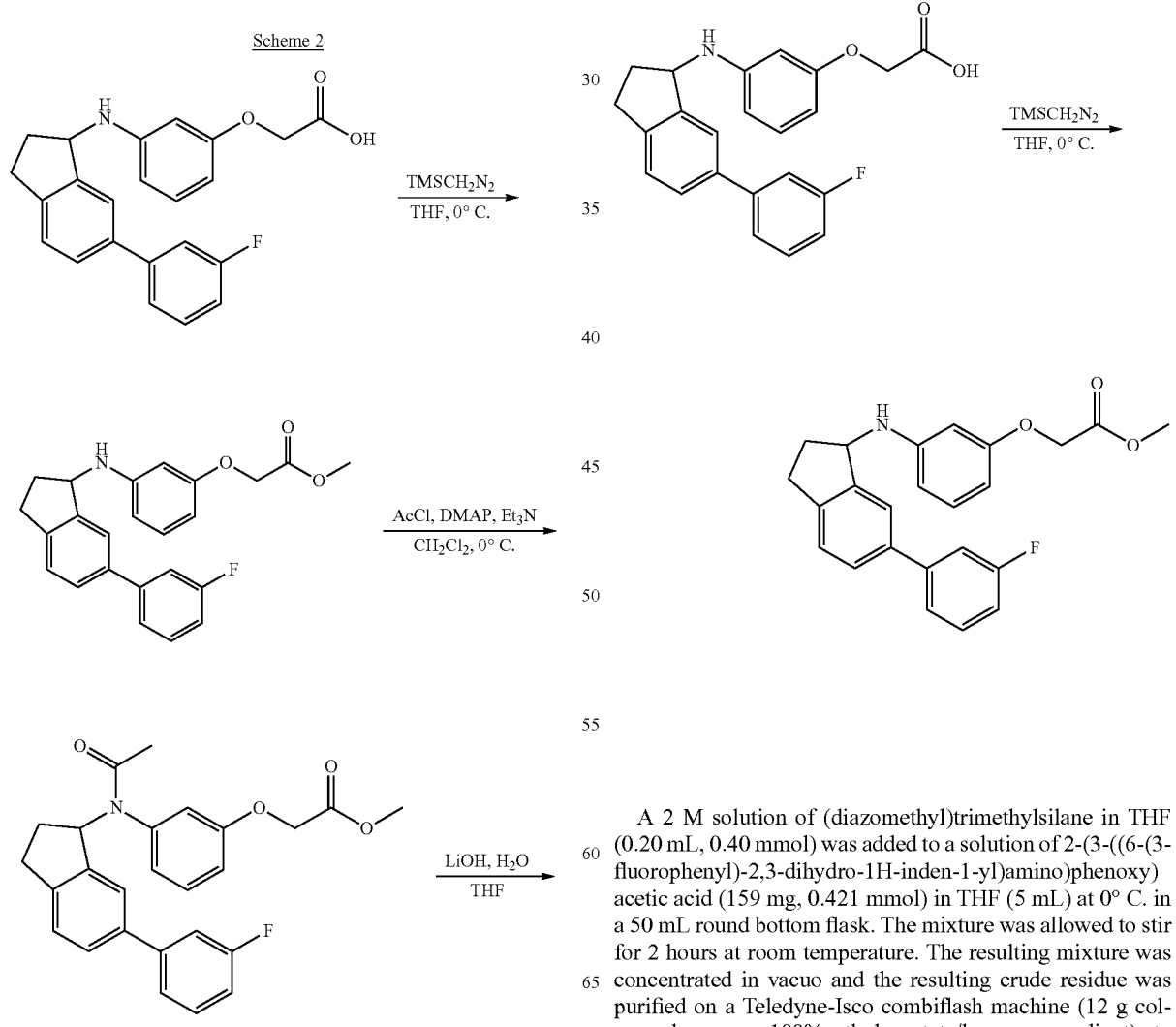

Scheme 2

A 2 M solution of (diazomethyl)trimethylsilane in THF (0.20 mL, 0.40 mmol) was added to a solution of 2-(3-((6-(3-fluorophenyl)-2,3-dihydro-1H-inden-1-yl)amino)phenoxy) acetic acid (159 mg, 0.421 mmol) in THF (5 mL) at 0° C. in a 50 mL round bottom flask. The mixture was allowed to stir for 2 hours at room temperature. The resulting mixture was concentrated in vacuo and the resulting crude residue was purified on a Teledyne-Isco combiflash machine (12 g column, hexanes→100% ethyl acetate/hexanes, gradient), to afford 135 mg (82%) of methyl 2-(3-((6-(3-fluorophenyl)-2,3-dihydro-1H-inden-1-yl)amino)phenoxy)acetate.

Step 2. Methyl 2-(3-(N-(6-(3-fluorophenyl)-2,3-dihydro-1H-inden-1-yl)acetamido)phenoxy)acetate

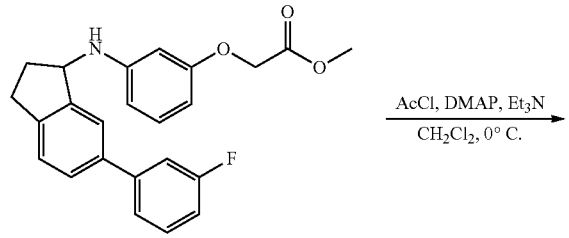

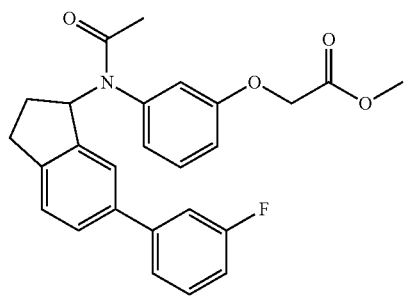

To a solution of methyl 2-(3-((6-(3-fluorophenyl)-2,3-dihydro-1H-inden-1-yl)amino)phenoxy)acetate (8 mg, 0.02 mmol) and dimethylaminopyridine (2 mg, 0.016 mmol) in dichloromethane (1 mL) at 0° C. was added acetyl chloride (12 mL, 0.173 mmol) and triethylamine (0.25 mL, 0.176 mmol). The reaction was warmed to room temperature and allowed to stir for approximately 2 hours. The resultant mixture was concentrated and the resulting crude residue was purified on a preparative TLC (1000 mm thickness) with a 1:1 ratio of ethyl acetate and hexane solution to afford 7 mg (94%) of methyl 2-(3-(N-(6-(3-fluorophenyl)-2,3-dihydro-1H-inden-1-yl)acetamido)phenoxy)acetate.

Step 3. 2-(3-(N-(6-(3-Fluorophenyl)-2,3-dihydro-1H-inden-1-yl)acetamido)phenoxy)acetic acid

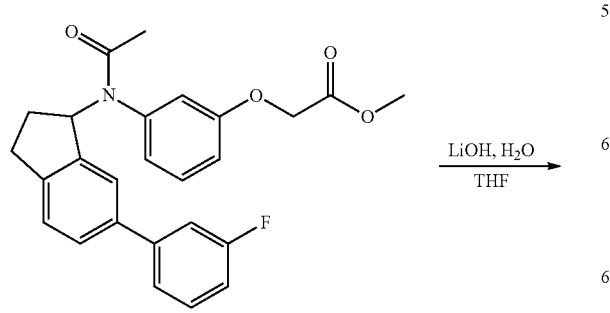

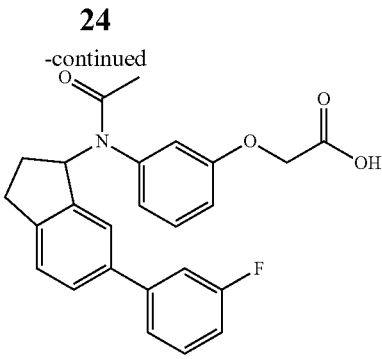

Aqueous lithium hydroxide (1 N, 1 mL, 1 mmol) was added to a solution of methyl 2-(3-(N-(6-(3-fluorophenyl)-2,3-dihydro-1H-inden-1-yl)acetamido)phenoxy)acetate (7 mg, 0.016 mmol) in THF (1 mL) in a scintillation vial. The vial was sealed and stirred overnight at room temperature. After 24 h, the reaction mixture was allowed to cool and the volatiles were concentrated. The residue was acidified with hydrochloric acid (1 N, 1 mL) and extracted with ethyl acetate (3×2 mL). The combined organic extracts were dried (Na$_2$SO$_4$), filtered and concentrated to afford 4 mg (59%) of the title compound.

Scheme 3

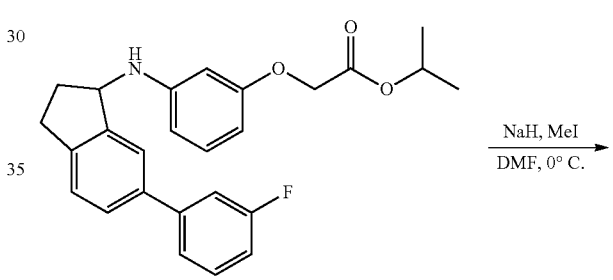

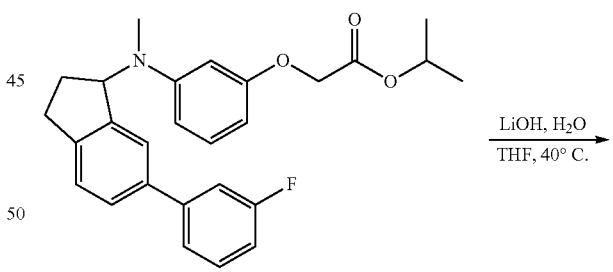

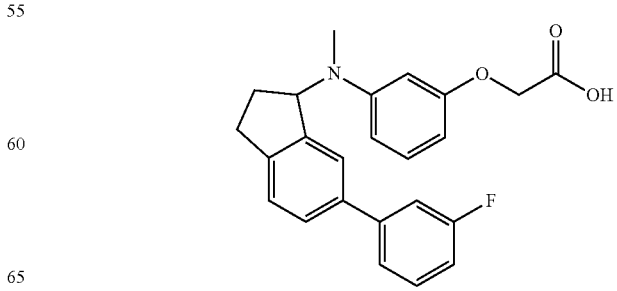

EXAMPLE 3

2-(3-((6-(3-Fluorophenyl)-2,3-dihydro-1H-inden-1-yl)(methyl)amino)phenoxy)acetic acid Step 1. Isopropyl 2-(3-((6-(3-fluorophenyl)-2,3-dihydro-1H-inden-1-yl)(methyl)amino)phenoxy)acetate

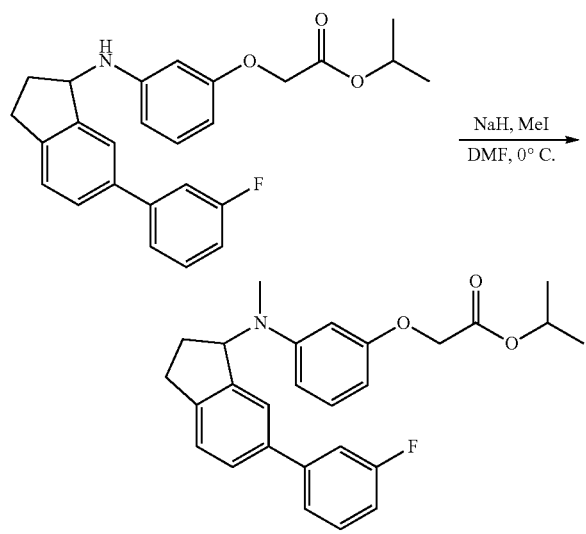

Methyl iodide (17 mg, 0.122 mmol) and sodium hydride (60% dispersion of mineral oil, 1.1 mg, 0.045 mmol) were added to a solution of isopropyl 2-(3-((6-(3-fluorophenyl)-2,3-dihydro-1H-inden-1-yl)amino)phenoxy)acetate (17 mg, 0.041 mmol) and dimethylformamide (2 mL) in a 50 mL round bottom flask at room temperature. The mixture was then heated to 50° C. and allowed to stir overnight. The solution was quenched with saturated ammonium chloride (25 mL) and extracted with ethyl acetate (100 mL). The organic layer was washed with brine (1×100 mL). The combined organic extracts were dried (Na$_2$SO$_4$), filtered and concentrated. The resulting crude residue was purified by preparative TLC (1000 mm thickness, 30% ethyl acetate/hexanes) to afford 12 mg (68%) of isopropyl 2-(3-((6-(3-fluorophenyl)-2,3-dihydro-1H-inden-1-yl)(methyl)amino)phenoxy)acetate.

Step 2. 2-(3-((6-(3-Fluorophenyl)-2,3-dihydro-1H-inden-1-yl)(methyl)amino)phenoxy)acetic acid

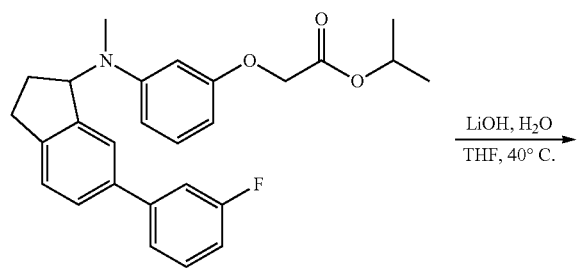

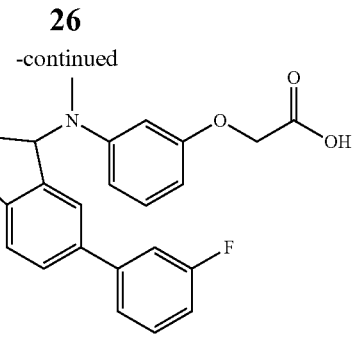

Aqueous lithium hydroxide (1 N, 1 mL, 1 mmol) was added to a solution of isopropyl 2-(3-((6-(3-fluorophenyl)-2,3-dihydro-1H-inden-1-yl)(methyl)amino)phenoxy)acetate (12 mg, 0.028 mmol) in THF (1 mL) in a scintillation vial. The vial was sealed and stirred overnight at room temperature. After 24 h, the reaction mixture was allowed to cool and the volatiles were concentrated. The residue was acidified with hydrochloric acid (1 N, 1 mL) and extracted with ethyl acetate (3×2 mL). The combined organic extracts were dried (Na$_2$SO$_4$), filtered and concentrated. The resulting crude residue was purified by preparative TLC (1000 mm thickness, 10% methanol/dichloromethane) to afford 7 mg (65%) of the title compound.

Scheme 4

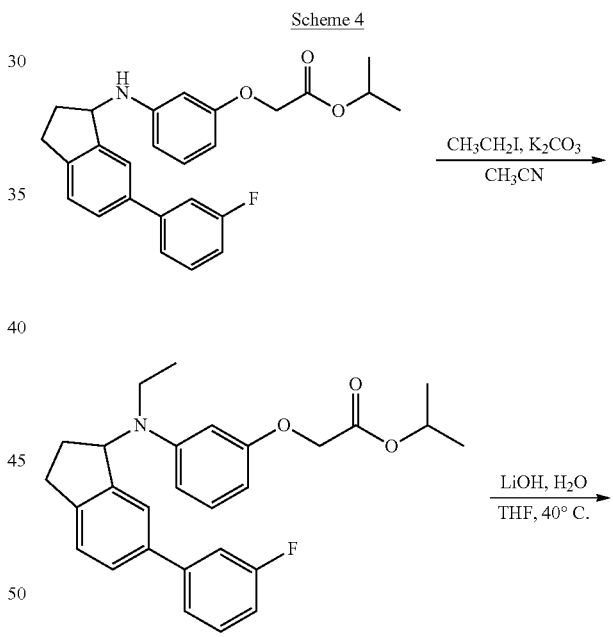

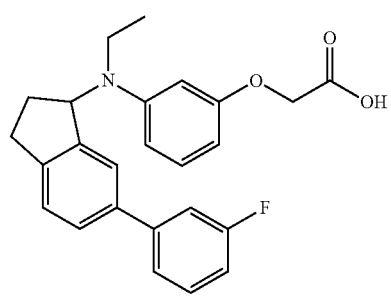

EXAMPLE 4

2-(3-(Ethyl(6-(3-fluorophenyl)-2,3-dihydro-1H-inden-1-yl)amino)phenoxy)acetic acid Step 1. Isopropyl 2-(3-(ethyl(6-(3-fluorophenyl)-2,3-dihydro-1H-inden-1-yl)amino)phenoxy)acetate

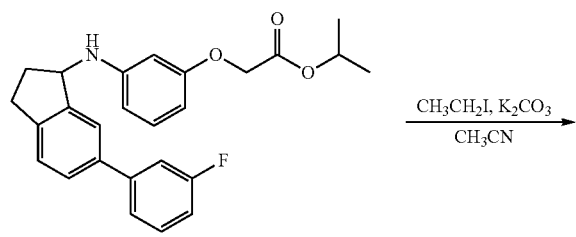

Ethyl iodide (45 mg, 0.286 mmol) and potassium carbonate (8 mg, 0.057 mmol) were added to a solution of isopropyl 2-(3-((6-(3-fluorophenyl)-2,3-dihydro-1H-inden-1-yl)amino)phenoxy)acetate (12 mg, 0.029 mmol) and acetonitrile (2 mL) in a 50 mL round bottom flask at room temperature. The mixture was then heated to reflux and allowed to stir overnight. The solution was quenched with saturated ammonium chloride (5 mL) and extracted with ethyl acetate (50 mL). The combined organic extracts were dried ($Na_2SO_4$), filtered and concentrated. The resulting crude residue was purified by preparative TLC (1000 mm thickness, 50% ethyl acetate/hexanes) to afford 7 mg (55%) of isopropyl 2-(3-(ethyl(6-(3-fluorophenyl)-2,3-dihydro-1H-inden-1-yl)amino)phenoxy)acetate.

Step 2. 2-(3-(Ethyl(6-(3-fluorophenyl)-2,3-dihydro-1H-inden-1-yl)amino)phenoxy)acetic acid

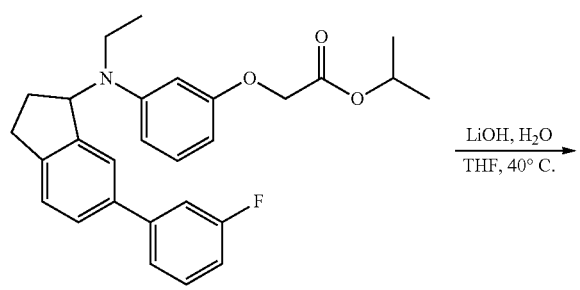

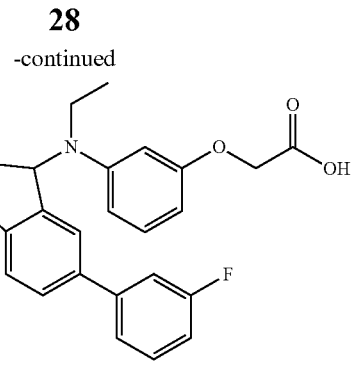

Aqueous lithium hydroxide (1 N, 1 mL, 1 mmol) was added to a solution of isopropyl 2-(3-(ethyl(6-(3-fluorophenyl)-2,3-dihydro-1H-inden-1-yl)amino)phenoxy)acetate (7 mg, 0.016 mmol) in THF (1 mL) in a scintillation vial. The vial was sealed and stirred overnight at room temperature. After 24 h, the reaction mixture was allowed to cool and the volatiles were concentrated. The residue was acidified with hydrochloric acid (1 N, 1 mL) and extracted with ethyl acetate (3×2 mL). The combined organic extracts were dried ($Na_2SO_4$), filtered and concentrated. The resulting crude residue was purified by preparative TLC (1000 mm thickness, 10% methanol/dichloromethane) to afford 2 mg (32%) of the title compound.

Scheme 5

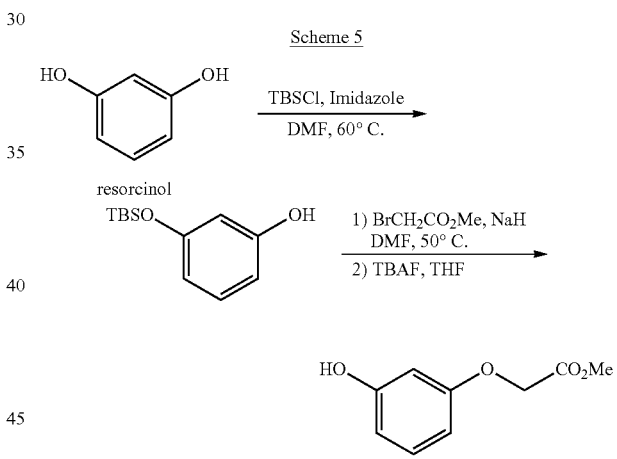

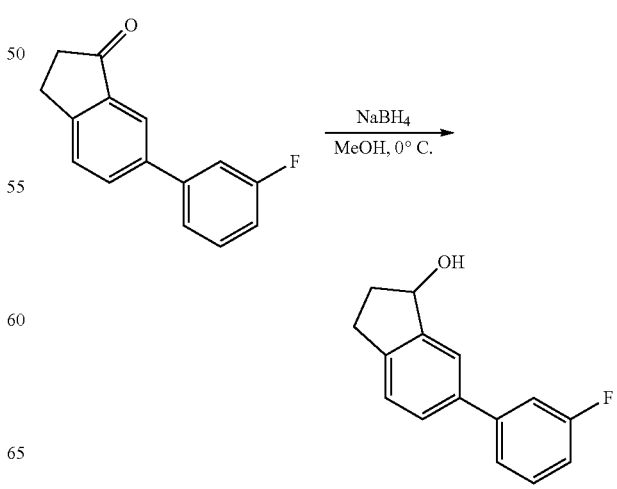

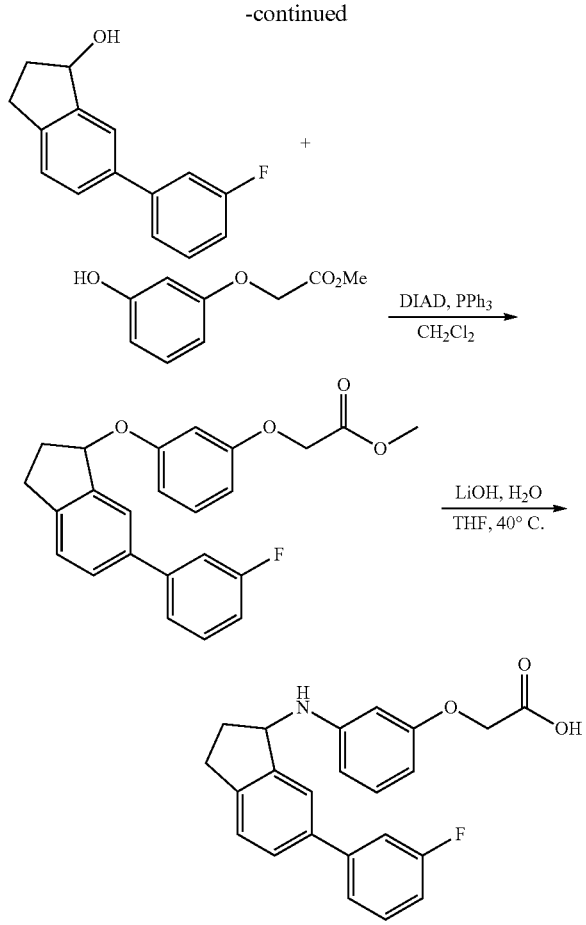

EXAMPLE 5

2-(3-((6-(3-Fluorophenyl)-2,3-dihydro-1H-inden-1-yl)oxy)phenoxy)acetic acid

Step 1. 3-((t-Butyldimethylsilyl)oxy)phenol

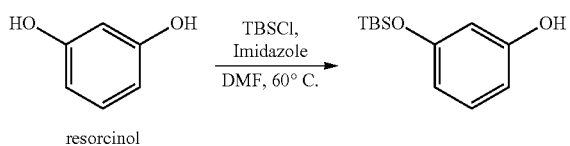

Imidazole (4.3 g, 62 mmol) and t-butyldimethylsilylchloride (5.5 g, 36 mmol) were added to a solution of resorcinol (2.8 g, 25 mmol) and dimethylformamide (100 mL) in a 250 mL round bottom flask under a nitrogen atmosphere at room temperature. The solution was heated in a 60° C. oil bath and allowed to stir for 2 hours. The resulting mixture was cooled to room temperature. The reaction was quenched with saturated aqueous ammonium chloride (100 mL) and extracted with ethyl acetate (3×200 mL). The combined organic extracts were dried (Na$_2$SO$_4$), filtered and concentrated. The resulting crude residue was purified by combiflash (40 g column, hexanes→100% ethyl acetate/hexanes, gradient) to afford 2.7 g (48%) of 3-((t-butyldimethylsilyl)oxy)phenol.

Step 2. Methyl 2-(3-((t-butyldimethylsilyl)oxy)phenoxy)acetate

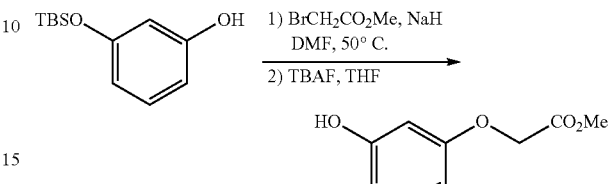

Sodium hydride (60% mineral oil dispersion, 0.35 g, 8.7 mmol) was added to a solution of 3-((t-butyldimethylsilyl)oxy)phenol (0.49 g, 2.2 mmol), methyl 2-bromoacetate (0.37 g, 2.4 mmol), and dimethylformamide (2 mL) in a 50 mL round bottom flask under a nitrogen atmosphere at room temperature. The solution was heated in a 50° C. oil bath and allowed to stir overnight for approximately 16 hours. The resulting mixture was cooled to room temperature. The reaction was quenched with saturated aqueous ammonium chloride (100 mL) and extracted with ethyl acetate (200 mL). The organic extract was dried (Na$_2$SO$_4$), filtered and concentrated. The resulting crude residue was purified by combiflash (40 g column, hexanes→100% ethyl acetate/hexanes, gradient) to afford 0.5 g (77%) of methyl 2-(3-((t-butyldimethylsilyl)oxy)phenoxy)acetate.

Step 3. Methyl 2-(3-hydroxyphenoxy)acetate

Tetrabutylammonium fluoride in THF (1 M, 3.4 mL, 3.4 mmol) was added to a solution of methyl 2-(3-((t-butyldimethylsilyl)oxy)phenoxy)acetate (0.50 g, 1.7 mmol) in THF (5 mL) in a 100 mL round bottom flask. The reaction was allowed to stir overnight at room temperature. The reaction was quenched with saturated aqueous ammonium chloride (100 mL) and extracted with ethyl acetate (200 mL). The organic extract was dried (Na$_2$SO$_4$), filtered and concentrated. The resulting crude residue was purified by combiflash (40 g column, hexanes→100% ethyl acetate/hexanes, gradient) to afford 0.19 g (60%) of methyl 2-(3-hydroxyphenoxy)acetate.

Step 4. 6-(3-Fluorophenyl)-2,3-dihydro-1H-inden-1-ol

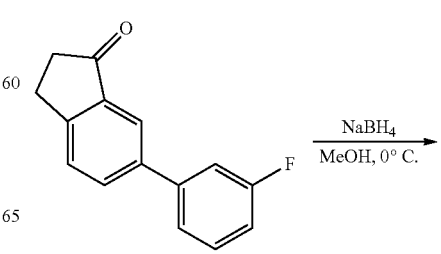

-continued

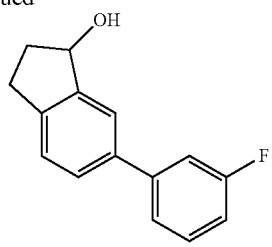

Sodium borohyride (19 mg, 0.5 mmol) was added to a solution of 6-(3-fluorophenyl)-2,3-dihydro-1H-inden-1-one (55 mg, 0.24 mmol) and methanol (12 mL) in a 100 mL round bottom flask at 0° C. After stirring for 1 hour, the resulting mixture was warmed to room temperature. The reaction was quenched with saturated aqueous ammonium chloride (100 mL) and extracted with ethyl acetate (100 mL). The organic extract was dried (Na$_2$SO$_4$), filtered and concentrated. The resulting crude residue was purified by combiflash (4 g column, hexanes→100% ethyl acetate/hexanes, gradient) to afford 55 mg (99%) of 6-(3-fluorophenyl)-2,3-dihydro-1H-inden-1-ol.

Step 5. Methyl 2-(3-((6-(3-fluorophenyl)-2,3-dihydro-1H-inden-1-yl)oxy)phenoxy)acetate

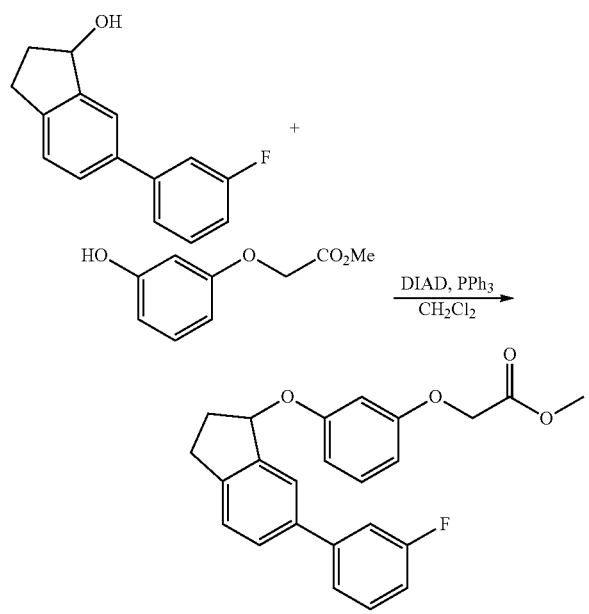

Diisopropyl azodicarboxylate (57 mg, 0.28 mmol) was added to a solution of 6-(3-fluorophenyl)-2,3-dihydro-1H-inden-1-ol (55 mg, 0.24 mmol), triphenylphosphine (97 mg, 0.37 mmol), methyl 2-(3-hydroxyphenoxy)acetate (37 mg, 0.20 mmol) and dichloromethane (2 mL) in a 50 mL round bottom flask at room temperature. After stirring overnight for 16 hours, the resulting mixture was quenched with saturated aqueous NaHCO$_3$ (50 mL) and extracted with ethyl acetate (100 mL). The combined organic extracts were dried (Na$_2$SO$_4$), filtered and concentrated. The resulting crude residue was purified by combiflash (4 g column, hexanes→100% ethyl acetate/hexanes, gradient) to afford 38 mg (40%) of methyl 2-(3-((6-(3-fluorophenyl)-2,3-dihydro-1H-inden-1-yl)oxy)phenoxy)acetate.

Step 6. 2-(3-((6-(3-Fluorophenyl)-2,3-dihydro-1H-inden-1-yl)oxy)phenoxy)acetic acid

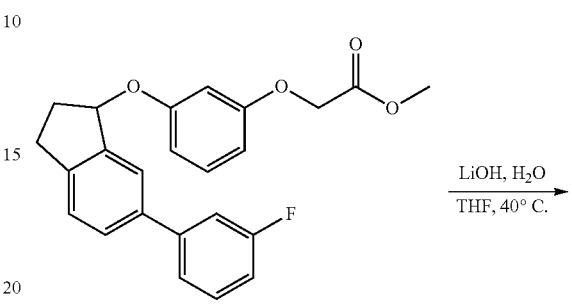

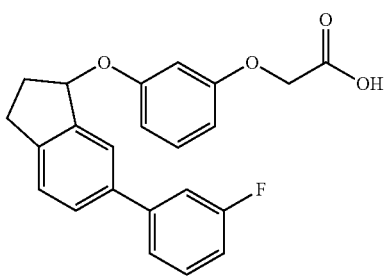 [SMILES: O=C(O)COc1cccc(NC2CCc3ccc(-c4cccc(F)c4)cc32)c1]

Aqueous lithium hydroxide (1 N, 1 mL, 1 mmol) was added to a solution of methyl 2-(3-((6-(3-fluorophenyl)-2,3-dihydro-1H-inden-1-yl)oxy)phenoxy)acetate (38 mg, 0.091 mmol) in THF (1 mL) in a scintillation vial. The vial was sealed and stirred overnight at 40° C. After 24 h, the reaction mixture was allowed to cool and the volatiles were concentrated. The residue was acidified with hydrochloric acid (1 N, 1 mL) and extracted with ethyl acetate (3×2 mL). The combined organic extracts were dried (Na$_2$SO$_4$), filtered and concentrated. The resulting crude residue was purified by preparative TLC (1000 mm thickness, 15% methanol/dichloromethane) to afford 21 mg (61%) of the title compound.

Scheme 6

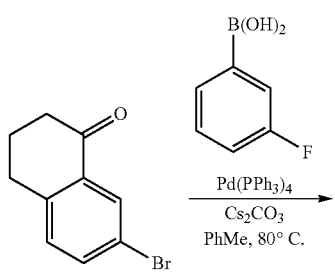

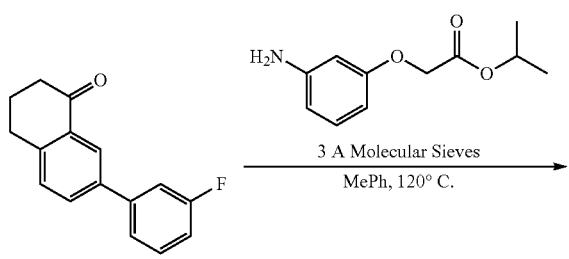

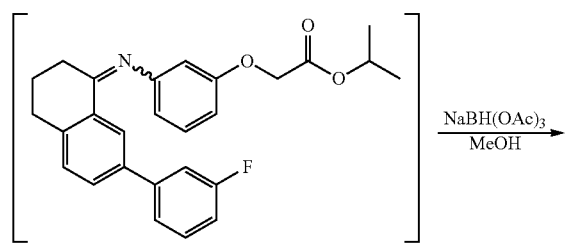

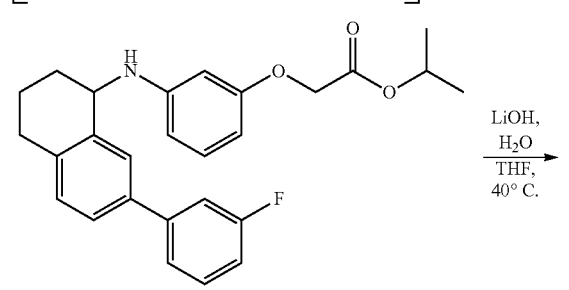

EXAMPLE 6

2-(3-((7-(3-Fluorophenyl)-1,2,3,4-tetrahydronaphthalen-1-yl)amino)phenoxy)acetic acid

Step 1.
7-(3-Fluorophenyl)-3,4-dihydronaphthalen-1(2H)-one

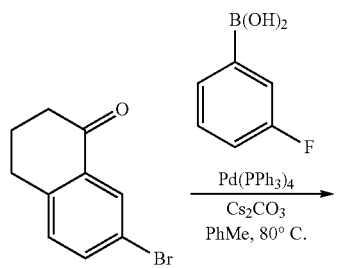

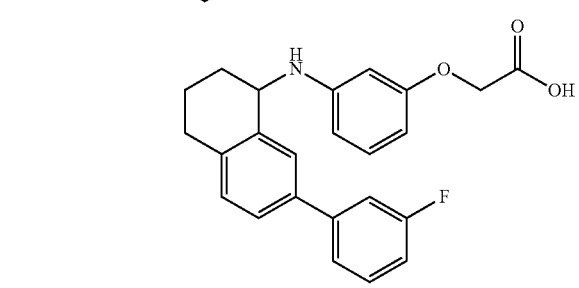

Cesium carbonate (869 mg, 2.67 mmol) was added to a solution of 7-bromo-3,4-dihydronaphthalen-1(2H)-one (300 mg, 1.33 mmol), (3-fluorophenyl) boronic acid (372 mg, 2.67 mmol) and toluene (20 mL) in a 50 mL Schlenk tube. A nitrogen atmosphere was established by evacuating and refilling with nitrogen (3×), then tetrakis(triphenylphosphine)palladium (0) (15 mg, 0.013 mmol) was added to the reaction. The flask was sealed and heated in a 80° C. oil bath overnight. The resulting mixture was cooled to room temperature. The reaction was then diluted with ethyl acetate and filtered through celite. Ethyl acetate (30 mL) was used to wash the flask and the combined organic filtrate was concentrated. The resulting crude residue was purified on a Teledyne-Isco Combiflash machine (40 g column, hexanes→100% ethyl acetate/hexanes, gradient), to afford 174 mg (54%) of 7-(3-fluorophenyl)-3,4-dihydronaphthalen-1(2H)-one.

Step 2. Isopropyl 2-(3-((7-(3-fluorophenyl)-3,4-dihydronaphthalen-1(2H)-ylidene)amino)phenoxy)acetate Approximately forty oven dried 3 Å molecular sieves were added to a solution of 7-(3-fluorophenyl)-3,4-dihydronaphthalen-1(2H)-one (174 mg, 0.724 mmol) and isopropyl 2-(3-aminophenoxyl)acetate (644 mg, 3.08 mmol) in toluene (15 mL) at 25° C. The reaction was heated in an 120° C. oil bath and allowed to stir overnight for approximately 16 hours. The reaction was cooled to room temperature and concentrated. The resulting crude residue was purified by combiflash (4 g column, hexanes→100% ethyl acetate/hexanes, gradient) to afford 25 mg (4%) of isopropyl 2-(3-((7-(3-fluorophenyl)-3,4-dihydronaphthalen-1(2H)-ylidene)amino)phenoxy)acetate.

Step 3. Isopropyl 2-(3-((7-(3-fluorophenyl)-1,2,3,4-tetrahydronaphthalen-1-yl)amino)phenoxy)acetate

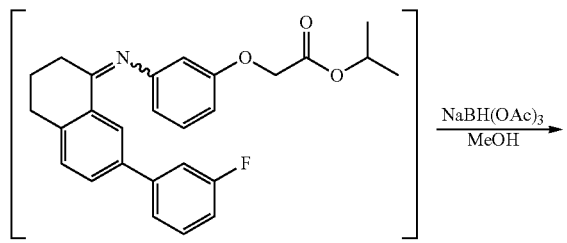

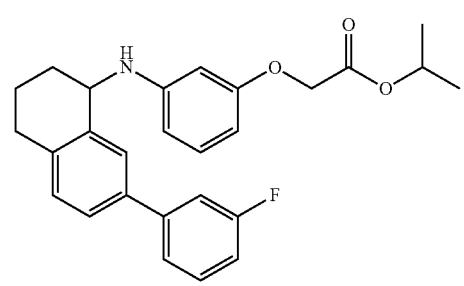

To a solution of isopropyl 2-(3-((7-(3-fluorophenyl)-3,4-dihydronaphthalen-1(2H)-ylidene)amino)phenoxy)acetate (25 mg, 0.057 mmol) and methanol (2 mL) was added sodium triacetoxyborohyride (12 mg, 0.057 mmol) at 0° C. The solution was stirred for 4 hours at room temperature. The reaction was quenched with saturated aqueous NaHCO₃ (50 mL) and extracted with ethyl acetate (3×50 mL). The combined organic extracts were dried (Na₂SO₄), filtered and concentrated. The resulting crude residue was purified by combiflash (4 g column, hexanes→100% ethyl acetate/hexanes, gradient) to afford 9 mg (36%) of isopropyl 2-(3-((7-(3-fluorophenyl)-1,2,3,4-tetrahydronaphthalen-1-yl)amino)phenoxy)acetate.

Step 4. 2-(3-((7-(3-Fluorophenyl)-1,2,3,4-tetrahydronaphthalen-1-yl)amino)phenoxy)acetic acid

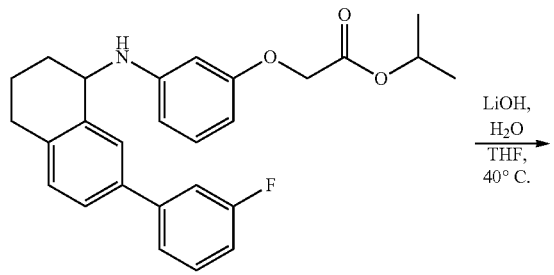

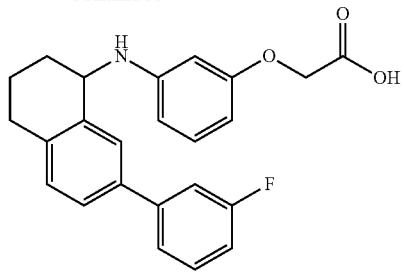

Aqueous lithium hydroxide (1 N, 1 mL, 1 mmol) was added to a solution of isopropyl 2-(3-((7-(3-fluorophenyl)-1,2,3,4-tetrahydronaphthalen-1-yl)amino)phenoxy)acetate (5 mg, 0.012 mmol) in THF (1 mL) in a scintillation vial. The vial was sealed and heated at 40° C. After 24 h, the reaction mixture was allowed to cool and the volatiles were concentrated in vacuo. The residue was acidified with hydrochloric acid (1 N, 1 mL), and extracted with ethyl acetate (3×2 mL). The combined organic extracts were dried (Na₂SO₄), filtered and concentrated to afford 3 mg (66%) of the title compound.

Scheme 7

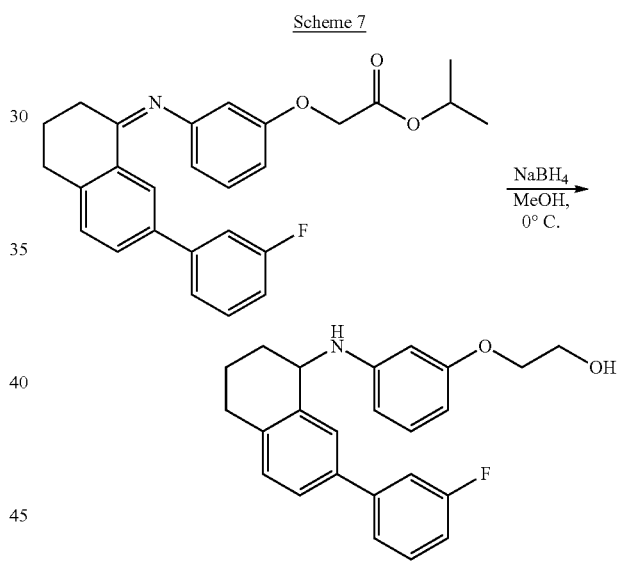

EXAMPLE 7

2-(3-((7-(3-Fluorophenyl)-1,2,3,4-tetrahydronaphthalen-1-yl)amino)phenoxy)ethanol To a solution of isopropyl 2-(3-((7-(3-fluorophenyl)-3,4-dihydronaphthalen-1(2H)-ylidene)amino)phenoxy)acetate (4 mg, 0.01 mmol) and THF (1 mL) was added sodium borohyride (22 mg, 0.58 mmol) at 0° C. The solution was stirred for 4 hours at room temperature. The reaction was quenched with saturated aqueous NaHCO₃ (50 mL) and extracted with ethyl acetate (3×50 mL). The combined organic extracts were dried (Na₂SO₄), filtered and concentrated. The resulting crude residue was purified by combiflash (4 g column, hexanes→100% ethyl acetate/hexanes, gradient) to afford 3 mg (82%) of the title compound.

Scheme 8

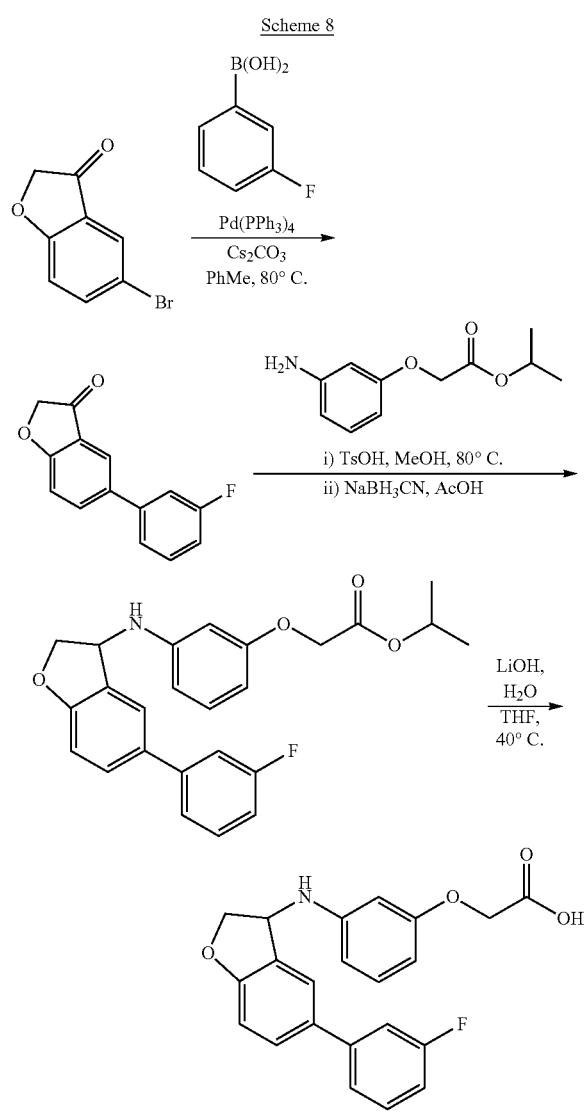

EXAMPLE 8

2-(3-((5-(3-Fluorophenyl)-2,3-dihydrobenzofuran-3-yl)amino)phenoxy)acetic acid

Step 1. 5-(3-Fluorophenyl)benzofuran-3(2H)-one

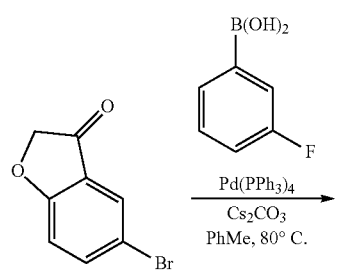

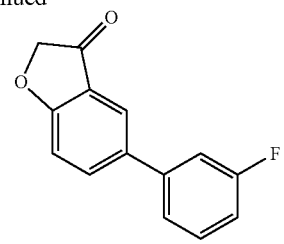

Cesium carbonate (612 mg, 1.88 mmol) was added to a solution of 5-bromobenzofuran-3(2H)-one (200 mg, 0.939 mmol), (3-fluorophenyl)boronic acid (263 mg, 1.88 mmol) and toluene (20 mL) in a 50 mL Schlenk tube. A nitrogen atmosphere was established by evacuating and refilling with nitrogen (3×), then tetrakis(triphenylphosphine)palladium (0) (11 mg, 0.01 mmol) was added to the reaction. The flask was sealed and heated in a 80° C. oil bath overnight. The resulting mixture was cooled to room temperature. The reaction was then diluted with ethyl acetate and filtered through celite. Ethyl acetate (30 mL) was used to wash the flask and the combined organic filtrate was concentrated. The resulting crude residue was purified on a Teledyne-Isco Combiflash machine (40 g column, hexanes→100% ethyl acetate/hexanes, gradient), to afford 212 mg (99%) of 5-(3-fluorophenyl)benzofuran-3(2H)-one.

Step 2. Isopropyl 2-(3-((5-(3-fluorophenyl)-2,3-dihydrobenzofuran-3-yl)amino)phenoxy)acetate

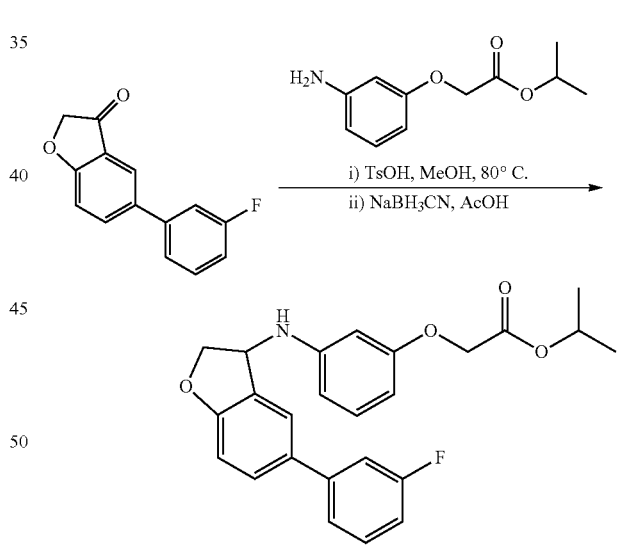

Para-toluenesulfonic acid (76 mg, 0.43 mmol) was added to a solution of 5-(3-fluorophenyl)benzofuran-3(2H)-one (212 mg, 0.935 mmol) and isopropyl 2-(3-aminophenoxyl)acetate (202 mg, 0.964 mmol) in methanol (4 mL) at 25° C. The reaction was heated in an 80° C. oil bath and allowed to stir overnight for approximately 16 hours. The reaction was cooled to room temperature and concentrated in vacuo. The mixture was then dissolved in concentrated acetic acid (2 mL) and cooled to 0° C. Sodium cyanoborohydride (386 mg, 6.13 mmol) was added and the solution was stirred for 4 hours at room temperature. The reaction was quenched with saturated aqueous NaHCO₃ (50 mL) and extracted with ethyl acetate (3×50 mL). The combined organic extracts were dried (Na$_2$SO$_4$), filtered and concentrated. The resulting crude residue was purified by combiflash (12 g column, hexanes→100% ethyl acetate/hexanes, gradient) to afford 22 mg (6%) of isopropyl 2-(3-((5-(3-fluorophenyl)-2,3-dihydrobenzofuran-3-yl)amino)phenoxy)acetate.

Step 3. 2-(3-((5-(3-Fluorophenyl)-2,3-dihydrobenzofuran-3-yl)amino)phenoxy)acetic acid

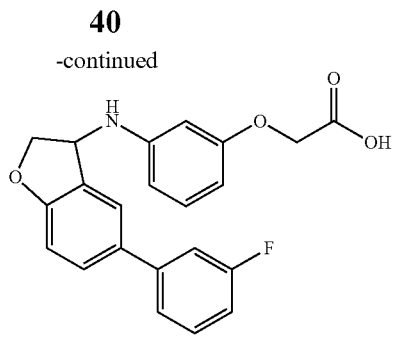

Aqueous lithium hydroxide (1 N, 1 mL, 1 mmol) was added to a solution of isopropyl 2-(3-((5-(3-fluorophenyl)-2,3-dihydrobenzofuran-3-yl)amino)phenoxy)acetate (22 mg, 0.052 mmol) in THF (1 mL) in a scintillation vial. The vial was sealed and heated at 40° C. After 24 h, the reaction mixture was allowed to cool and the volatiles were concentrated. The residue was acidified with hydrochloric acid (1 N, 1 mL), and extracted with ethyl acetate (3×2 mL). The combined organic extracts were dried (Na$_2$SO$_4$), filtered and concentrated to afford 11 mg (56%) of the title compound.

A person of ordinary skill in the art can prepare the subject compounds by using the methods disclosed herein, by adaptations readily ascertainable by those in the art from the disclosure herein, and/or by the knowledge generally available in the art as applied to the present disclosure.

In Vitro Testing

U.S. patent application publication No. 20070129552, published on Jun. 7, 2007, incorporated by reference herein, describes the methods used to obtain the in vitro data in Table 1 below.

TABLE 1

| Example No. | Structure | EP2 Data (EC50 in nM) cAMP | Ki | EP4 data (EC50 in nM) cAMP | KI | Other Receptors (EC50 in nM) hFP | hEP1 | hEP3A | hTP | hIP | hDP |
|---|---|---|---|---|---|---|---|---|---|---|---|
| 1 | | 11 | 80 | NA | 3045 | NA | NA | NA | NA | NA | NA |
| 2 | | NA | NA | NA | NA | NA | NA | NA | NA | NA | NA |

TABLE 1-continued

| Example No. | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 3 | | 697 | 1808 | NA | 7323 | NT | NT | NT | NT | NT | NT |
| 4 | | 8303 | 3935 | NA | 6639 | NT | NT | NT | NT | NT | NT |
| 5 | | 747 | 144 | NA | NA | NT | NT | NT | NT | NT | NT |
| 6 | | 438 | 104 | NA | 3632 | NT | NT | NT | NT | NT | NT |
| 7 | | NA | NA | NA | 6276 | NA | NA | NA | NA | NT | NA |

TABLE 1-continued

| Example No. | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 8 | 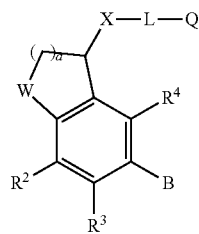 | 0.6 | 13 | NA | 7987 | NA | NA | NA | NA | NT | NA |

NA = Not Active
NT = Not Tested

Provided herein are the following non-limiting embodiments:

Embodiment 1. A Compound Represented by a Formula:

wherein B is optionally substituted phenyl;
W is $CH_2$, O, S, or NH;
a is 1 or 2;
X is $NR^1$ or O;
L is $-CH_2O-A$, $-CH_2CH_2-A-$, $-CH=CH-A-$, $-A-OCH_2-$, $-A-CH_2CH_2-$, or $-A-CH=CH-$;
A is an optionally substituted interarylene, an optionally substituted interheteroarylene, or $-(CH_2)_3-$;
$R^1$ is H, $C_{1-6}$ alkyl, or $COCH_3$;
$R^2$, $R^3$, and $R^4$ are independently H, or a substituent having a molecular weight of 15 g/mol to 100 g/mol; and
Q is $CO_2R^5$, $CH_2OR^5$, $CONR^5R^6$, or optionally substituted tetrazol-5-yl, wherein $R^5$ and $R^6$ are independently H, $C_{1-6}$ alkyl, $C_{1-6}$ hydroxyalkyl, or optionally substituted phenyl.

Embodiment 2. The compound of embodiment 1, wherein a is 1.

Embodiment 3. The compound of embodiment 1, wherein a is 2.

Embodiment 4. The compound of embodiment 1, 2, or 3, wherein $R^2$ is H.

Embodiment 5. The compound of embodiment 1, 2, 3, or 4, wherein $R^3$ is H.

Embodiment 6. The compound of embodiment 1, 2, 3, 4, or 5, wherein $R^4$ is H.

Embodiment 7. The compound of embodiment 1, 2, 3, 4, 5, or 6, wherein W is $CH_2$.

Embodiment 8. The compound of embodiment 1, 2, 3, 4, 5, or 6, wherein W is O.

Embodiment 9. The compound of embodiment 1, 2, 3, 4, 5, 6, 7, or 8, wherein X is $NR^1$.

Embodiment 10. The compound of embodiment 9, wherein $R^1$ is H.

Embodiment 11. The compound of embodiment 9, wherein $R^1$ is $C_{1-3}$ alkyl, or $COCH_3$.

Embodiment 12. The compound of embodiment 1, 2, 3, 4, 5, 6, 7, or 8, wherein X is O.

Embodiment 13. The compound of embodiment 1, 2, 3, 4, 5, 6, 7, 8, 9, 10, 11, or 12, wherein L is $-A-OCH_2-$.

Embodiment 14. The compound of embodiment 1, 2, 3, 4, 5, 6, 7, 8, 9, 10, 11, 12, or 13, wherein A is interphenylene.

Embodiment 15. The compound of embodiment 1, 2, 3, 4, 5, 6, 7, 8, 9, 10, 11, 12, 13, or 14, wherein Q is $CO_2R^5$.

Embodiment 16. The compound of embodiment 1, 2, 3, 4, 5, 6, 7, 8, 9, 10, 11, 12, 13, or 14, wherein Q is $CH_2OH$.

Embodiment 17. The compound of embodiment 1, 2, 3, 4, 5, 6, 7, 8, 9, 10, 11, 12, 13, 14, 15, or 16, wherein B is 3-fluorophenyl.

Embodiment 18. The compound of embodiment 1, further represented by a formula:

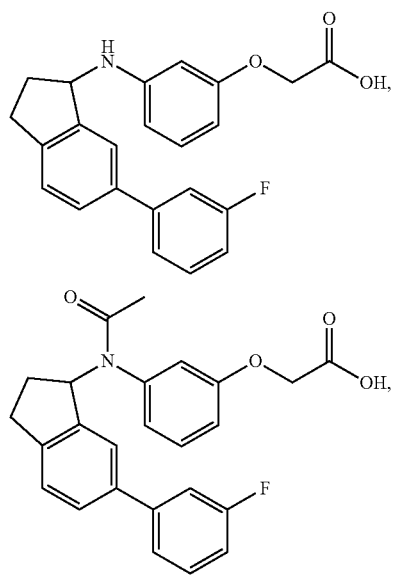

45
-continued

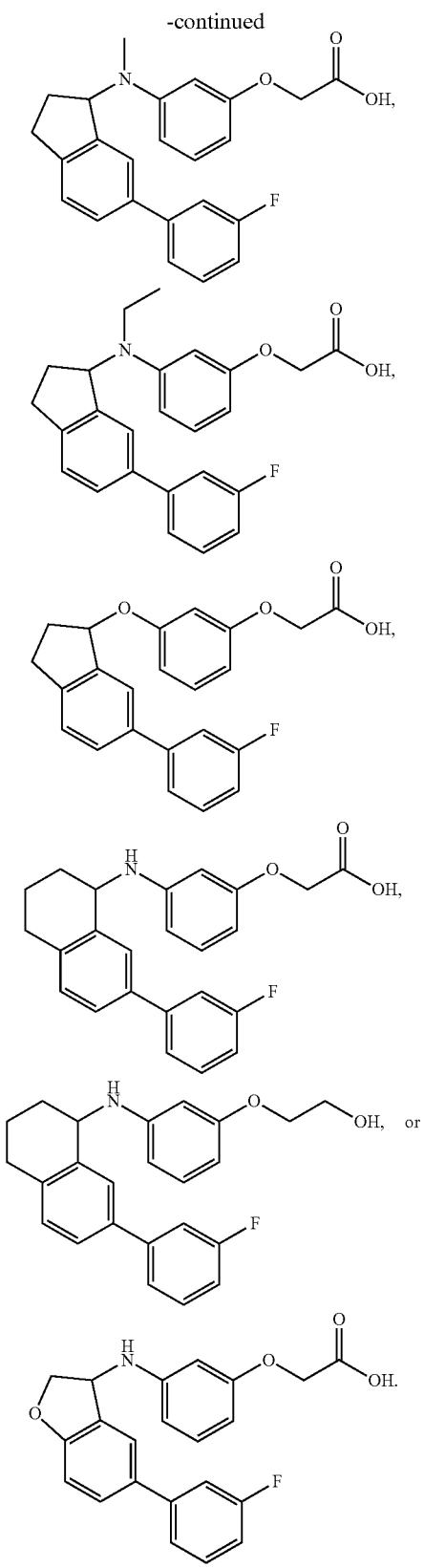

Embodiment 19. The compound according to any one of embodiments 1, 2, 3, 4, 5, 6, 7, 8, 9, 10, 11, 12, 13, 14, 15, 16, 17, or 18, wherein the compound binds to a prostaglandin receptor.

46

Embodiment 20. The compound of embodiment 19, wherein the compound binds to a prostaglandin EP2 receptor with a binding EC50 value of less than 200 nM.

Embodiment 21. The compound of embodiment 19 or 20, wherein the compound is a prostaglandin receptor agonist.

Embodiment 22. The compound of embodiment 21, wherein the compound is a prostaglandin EP2 receptor agonist with a functional EC50 value of less than 1000 nM.

Embodiment 23. The compound of embodiment 22, wherein the compound is more active at the prostaglandin EP2 receptor than at any other prostaglandin receptor.

Embodiment 24. An ophthalmic liquid comprising a compound according to any one of embodiments 1-23.

Embodiment 25. A solid dosage form comprising a compound according to any one of embodiments 1-23.

Embodiment 26. A method of reducing intraocular pressure comprising administering a compound according to any one of embodiments 1-23 to a mammal in need thereof.

Embodiment 27. A method or growing hair comprising administering a compound according to any one of embodiments 1-23 to a mammal in which hair growth is desirable.

The foregoing description details specific methods and compositions that can be employed to make and use the compounds described herein, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the scope of the claims.

What is claimed is:

1. A compound represented by a formula:

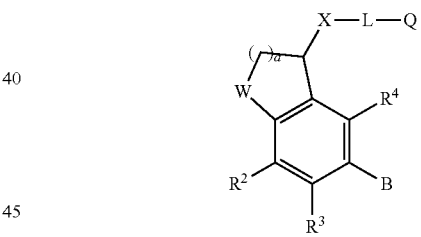

wherein B is optionally substituted phenyl;
W is $CH_2$, O, S, or NH;
a is 2;
X is $NR^1$ or O;
L is $-CH_2O-A-$, $-CH_2CH_2-A-$, $-CH=CH-A-$, $-A-OCH_2-$, $-A-CH_2CH_2-$, or $-A-CH=CH-$;
A is an optionally substituted interarylene, an optionally substituted interheteroarylene, or $-(CH_2)_3-$;
$R^1$ is H, $C_{1-6}$ alkyl, or $COCH_3$;
$R^2$, $R^3$, and $R^4$ are independently H, or a substituent having a molecular weight of 15 g/mol to 100 g/mol; and
Q is $CO_2R^5$, $CH_2OR^5$, $CONR^5R^6$, or optionally substituted tetrazol-5-yl, wherein $R^5$ and $R^6$ are independently H, $C_{1-6}$ alkyl, $C_{1-6}$ hydroxyalkyl, or optionally substituted phenyl.

2. The compound of claim 1, wherein $R^2$ is H.
3. The compound of claim 1, wherein $R^3$ is H.
4. The compound of claim 1, wherein $R^4$ is H.
5. The compound of claim 1, wherein W is $CH_2$.
6. The compound of claim 1, wherein W is O.

7. The compound of claim 1, wherein X is NR$^1$.

8. The compound of claim 7, wherein R$^1$ is H.

9. The compound of claim 7, wherein R$^1$ is C$_{1-3}$ alkyl, or COCH$_3$.

10. The compound of claim 1, wherein X is O.

11. The compound of claim 1, wherein L is -A-OCH$_2$—.

12. The compound of claim 1, wherein A is interphenylene.

13. The compound of claim 1, wherein Q is CO$_2$R$^5$.

14. The compound of claim 1, wherein Q is CH$_2$OH.

15. The compound of claim 1, wherein B is 3-fluorophenyl.

16. The compound selected from the group consisting of:

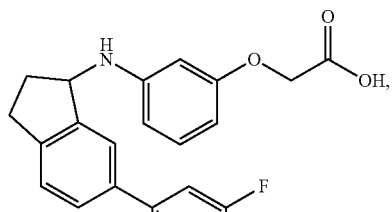

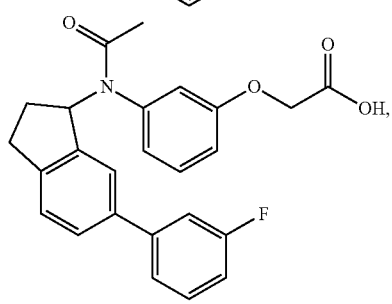

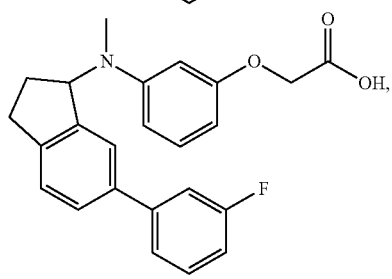

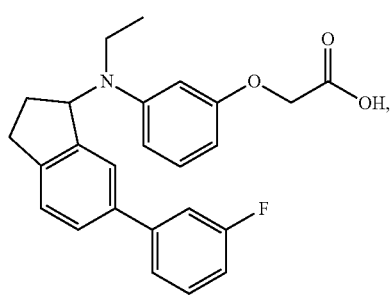 [SMILES: CCN(c1cccc(OCC(=O)O)c1)C1CCc2ccc(-c3cccc(F)c3)cc21]

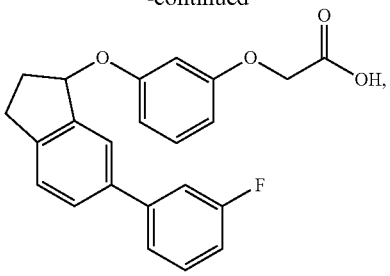

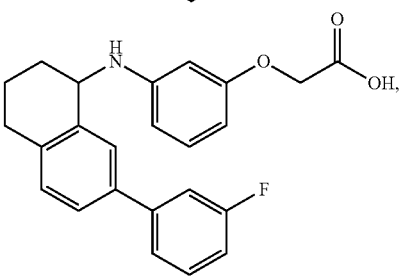

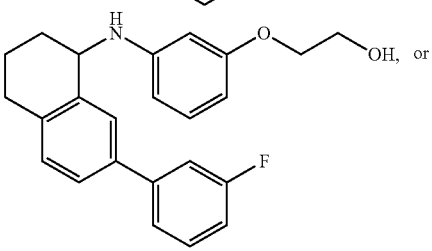

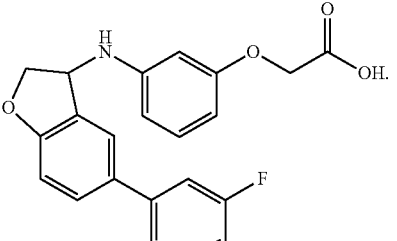

17. An ophthalmic liquid comprising a compound according to claim 1 and a pharmaceutically acceptable excipient.

18. A solid dosage form comprising a compound according to claim 1 and a pharmaceutically acceptable excipeint.

19. An ophthalmic liquid comprising a compound according to claim 16 and a pharmaceutically acceptable excipient.

20. A solid dosage form comprising a compound according to claim 16 and a pharmaceutically acceptable excipient.

21. A method of reducing intraocular pressure comprising administering a compound according to claim 1 to a mammal in need thereof.

22. A method or growing hair comprising administering a compound according to claim 1 to a mammal in which hair growth is desirable.

23. A method of reducing intraocular pressure comprising administering a compound according to claim 16 to a mammal in need thereof.

24. A method for growing hair comprising administering a compound according to claim 16 to a mammal in which hair growth is desirable.

* * * * *